(12) United States Patent
Scheller et al.

(10) Patent No.: US 9,480,600 B2
(45) Date of Patent: Nov. 1, 2016

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 804 days.

(21) Appl. No.: 13/896,500

(22) Filed: May 17, 2013

(65) Prior Publication Data

US 2014/0005642 A1 Jan. 2, 2014

Related U.S. Application Data

(60) Provisional application No. 61/665,079, filed on Jun. 27, 2012.

(51) Int. Cl.
*A61B 18/18* (2006.01)
*A61B 17/00* (2006.01)
(Continued)

(52) U.S. Cl.
CPC ........... *A61F 9/008* (2013.01); *A61F 9/00823* (2013.01); *A61B 2017/00318* (2013.01); *A61B 2018/00589* (2013.01); *A61B 2018/2238* (2013.01); *A61F 2009/00863* (2013.01)

(58) Field of Classification Search
CPC .... A61B 18/18; A61B 18/20; A61B 18/201; A61B 18/22; A61B 18/225; A61B 18/24; A61B 2018/2238; A61B 2018/0091; A61F 9/00823

USPC ...... 606/4–6, 13, 15, 16; 600/104, 108, 139, 600/140, 141, 142, 143, 144, 146–152
See application file for complete search history.

(56) References Cited

U.S. PATENT DOCUMENTS 5,190,050 A 3/1993 Nitzsche
5,355,871 A 10/1994 Hurley et al.
(Continued)

FOREIGN PATENT DOCUMENTS

EP    EP 0900547 B1    3/1999
WO   WO 2006/091597 A1   8/2006

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Anhtuan T Nguyen
*Assistant Examiner* — William Chou
(74) *Attorney, Agent, or Firm* — Kevin P. Rollins

(57) ABSTRACT

A steerable laser probe may include a handle having a handle distal end and a handle proximal end, a flexible housing tube having a flexible housing tube distal end and a flexible housing tube proximal end, an actuation mechanism control of the handle, and an optic fiber disposed within an inner bore of the handle and within the flexible housing tube. An actuation of the actuation mechanism control may be configured to gradually curve the flexible housing tube. A gradual curving of the flexible housing tube may be configured to gradually curve the optic fiber. An actuation of the actuation mechanism control may be configured to gradually straighten the flexible housing tube. A gradual straightening of the flexible housing tube may be configured to gradually straighten the optic fiber.

20 Claims, 26 Drawing Sheets

(51) Int. Cl.
    *A61B 1/00*     (2006.01)
    *A61M 25/00*     (2006.01)
    *A61F 9/008*     (2006.01)
    *A61B 18/00*     (2006.01)
    *A61B 18/22*     (2006.01)

(56) References Cited

U.S. PATENT DOCUMENTS

| | | | |
|---|---|---|---|
| 5,381,782 | A | 1/1995 | DeLaRama et al. |
| 5,439,000 | A | 8/1995 | Gunderson et al. |
| 5,454,794 | A | 10/1995 | Narciso et al. |
| 5,520,222 | A | 5/1996 | Chikama |
| 5,873,865 | A * | 2/1999 | Horzewski ........ A61M 25/0041 604/523 |
| 6,123,699 | A | 9/2000 | Webster, Jr. |
| 6,126,654 | A | 10/2000 | Giba et al. |
| 6,198,974 | B1 | 3/2001 | Webster, Jr. |
| 6,488,695 | B1 | 12/2002 | Hickingbotham |
| 6,505,530 | B2 | 1/2003 | Adler et al. |
| 6,530,913 | B1 | 3/2003 | Giba et al. |
| 6,551,302 | B1 | 4/2003 | Rosinko et al. |
| 6,572,608 | B1 | 6/2003 | Lee et al. |
| 6,620,153 | B2 | 9/2003 | Mueller et al. |
| 6,730,076 | B2 | 5/2004 | Hickingbotham |
| 6,863,668 | B2 | 3/2005 | Gillespie et al. |
| 6,984,230 | B2 | 1/2006 | Scheller et al. |
| 7,004,957 | B1 | 2/2006 | Dampney et al. |
| 7,226,444 | B1 * | 6/2007 | Ellman ................. A61B 18/22 606/15 |
| 7,303,533 | B2 | 12/2007 | Johansen et al. |
| 7,402,158 | B2 | 7/2008 | Scheller et al. |
| 7,632,242 | B2 | 12/2009 | Griffin et al. |
| 7,766,904 | B2 | 8/2010 | Mc Gowan, Sr. et al. |
| 8,038,692 | B2 | 10/2011 | Valencia et al. |
| 8,075,553 | B2 | 12/2011 | Scheller et al. |
| 8,197,468 | B2 | 6/2012 | Scheller et al. |
| 2003/0171762 | A1 | 9/2003 | Forchette et al. |
| 2004/0181138 | A1 | 9/2004 | Hindricks et al. |
| 2004/0249367 | A1 | 12/2004 | Saadat et al. |
| 2005/0054900 | A1 | 3/2005 | Mawn et al. |
| 2005/0154379 | A1 * | 7/2005 | McGowan ............ A61F 9/008 606/4 |
| 2005/0157985 | A1 | 7/2005 | McGowan, Sr. et al. |
| 2005/0272975 | A1 | 12/2005 | McWeeney et al. |
| 2007/0185514 | A1 | 8/2007 | Kirchhevel |
| 2008/0287938 | A1 * | 11/2008 | Scheller ................ A61B 18/22 606/15 |
| 2009/0018393 | A1 | 1/2009 | Dick et al. |
| 2009/0187170 | A1 | 7/2009 | Auld et al. |
| 2009/0312750 | A1 | 12/2009 | Spaide |
| 2010/0004642 | A1 | 1/2010 | Lumpkin |
| 2010/0268234 | A1 | 10/2010 | Aho et al. |
| 2011/0028947 | A1 | 2/2011 | Scheller et al. |
| 2012/0116361 | A1 | 5/2012 | Hanlon et al. |
| 2013/0035551 | A1 * | 2/2013 | Yu ....................... A61B 1/0052 600/141 |
| 2013/0060240 | A1 | 3/2013 | Scheller et al. |
| 2013/0071507 | A1 | 3/2013 | Scheller et al. |
| 2013/0096541 | A1 | 4/2013 | Scheller et al. |
| 2013/0116671 | A1 | 5/2013 | Scheller et al. |
| 2013/0150838 | A1 | 6/2013 | Scheller et al. |
| 2013/0165910 | A1 | 6/2013 | Scheller et al. |

\* cited by examiner

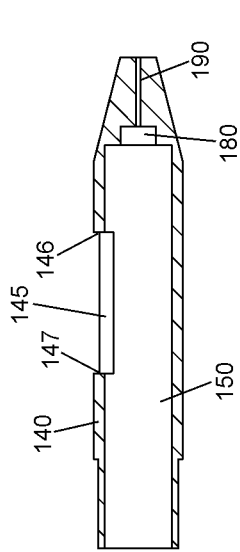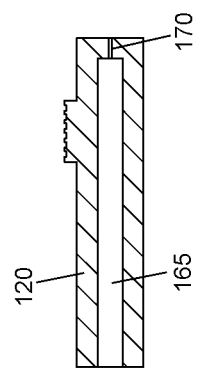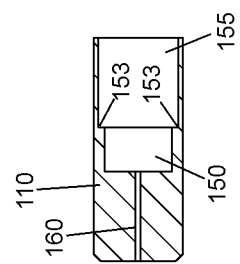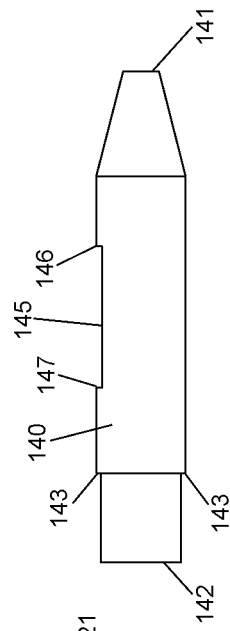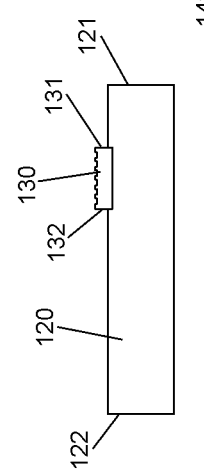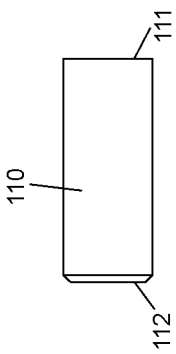
FIG. 1B
FIG. 1A

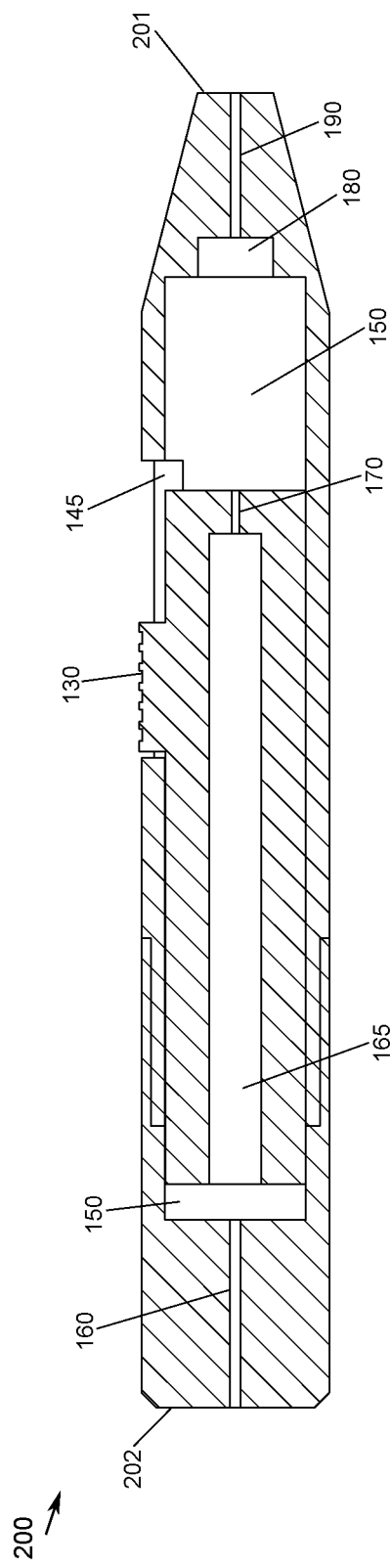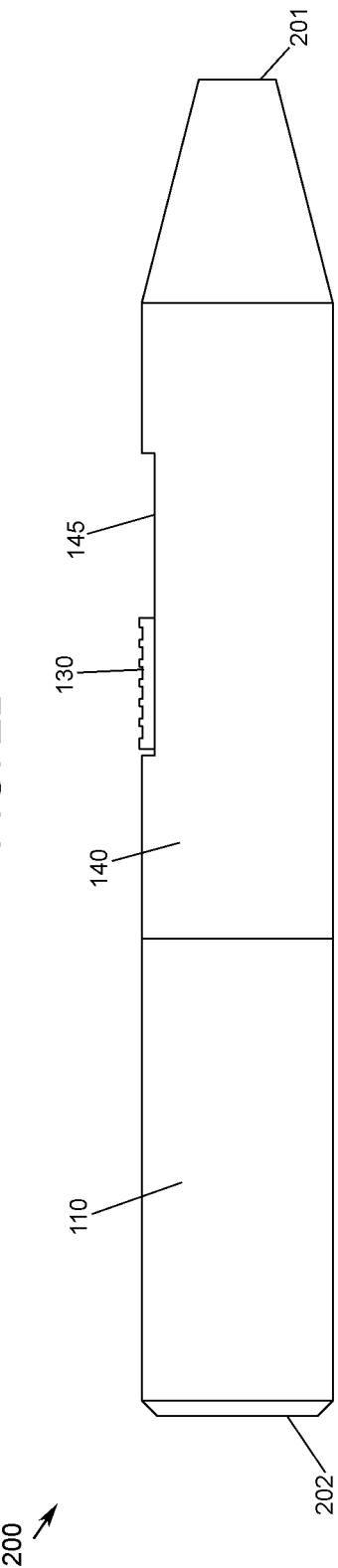
FIG. 2B
FIG. 2A

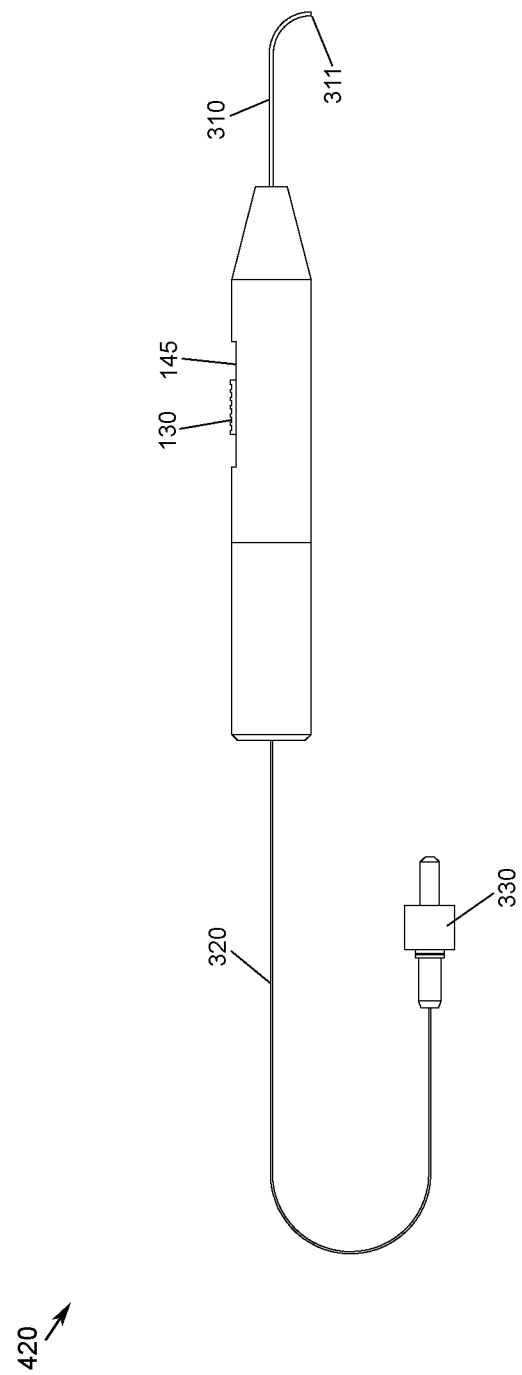

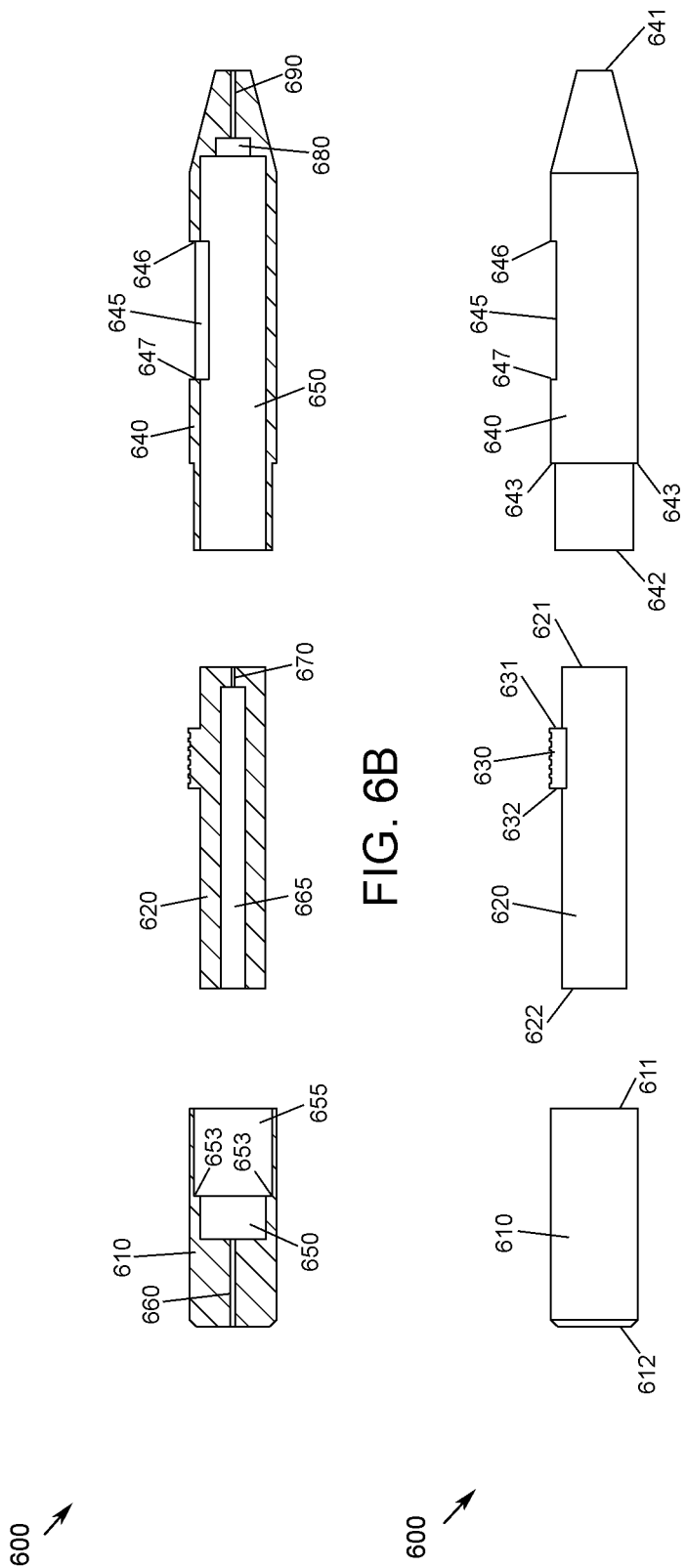

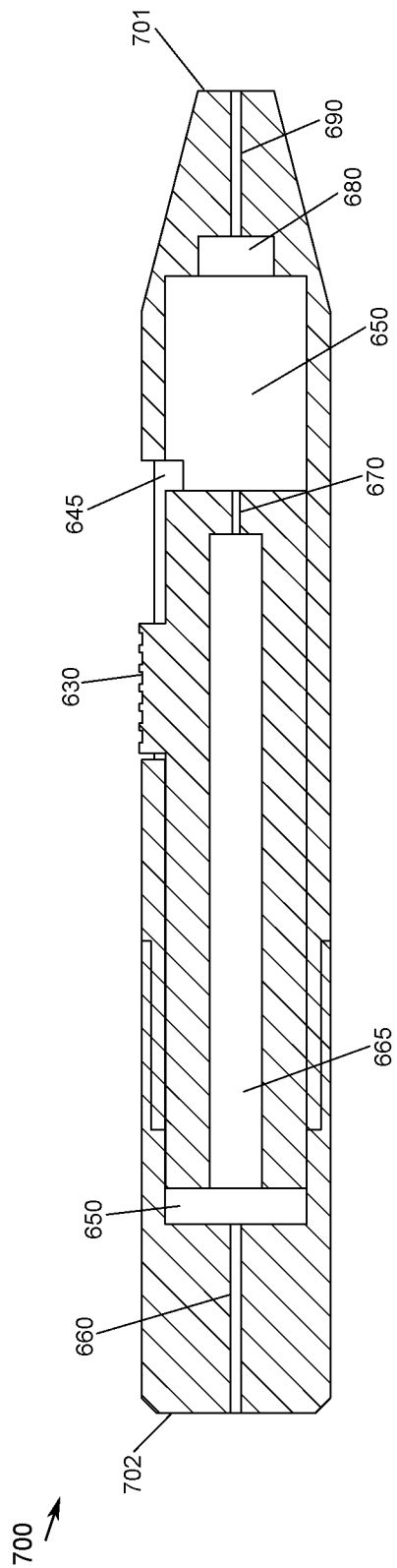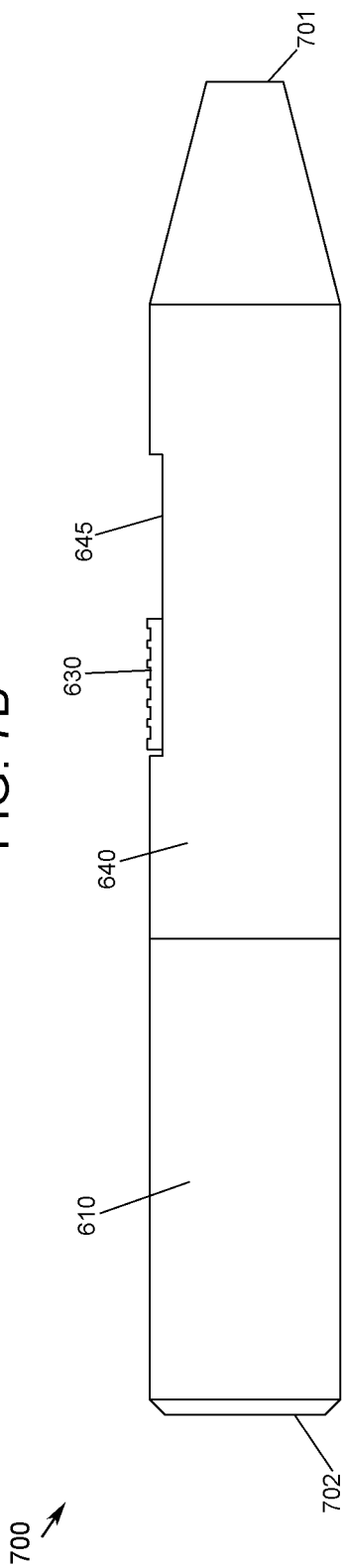
FIG. 7B
FIG. 7A

STEERABLE LASER PROBE

CROSS-REFERENCE TO RELATED APPLICATIONS

This application claims the benefit of U.S. Provisional Application No. 61/665,079, filed Jun. 27, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. In one or more embodiments, a steerable laser probe may comprise a handle having a handle distal end and a handle proximal end, a flexible housing tube having a flexible housing tube distal end and a flexible housing tube proximal end, an actuation mechanism control of the handle, and an optic fiber disposed within an inner bore of the handle and within the flexible housing tube. Illustratively, an actuation of the actuation mechanism control may be configured to gradually curve the flexible housing tube. In one or more embodiments, a gradual curving of the flexible housing tube may be configured to gradually curve the optic fiber. Illustratively, an actuation of the actuation mechanism control may be configured to gradually straighten the flexible housing tube. In one or more embodiments, a gradual straightening of the flexible housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating an exploded view of a handle assembly;

FIGS. 2A and 2B are schematic diagrams illustrating a handle;

FIGS. 4A, 4B, 4C, 4D, and 4E are schematic diagrams illustrating a gradual curving of an optic fiber;

FIGS. 6A and 6B are schematic diagrams illustrating an exploded view of a handle assembly;

FIGS. 7A and 7B are schematic diagrams illustrating a handle;

DETAILED DESCRIPTION OF AN ILLUSTRATIVE EMBODIMENT

Figure 3:
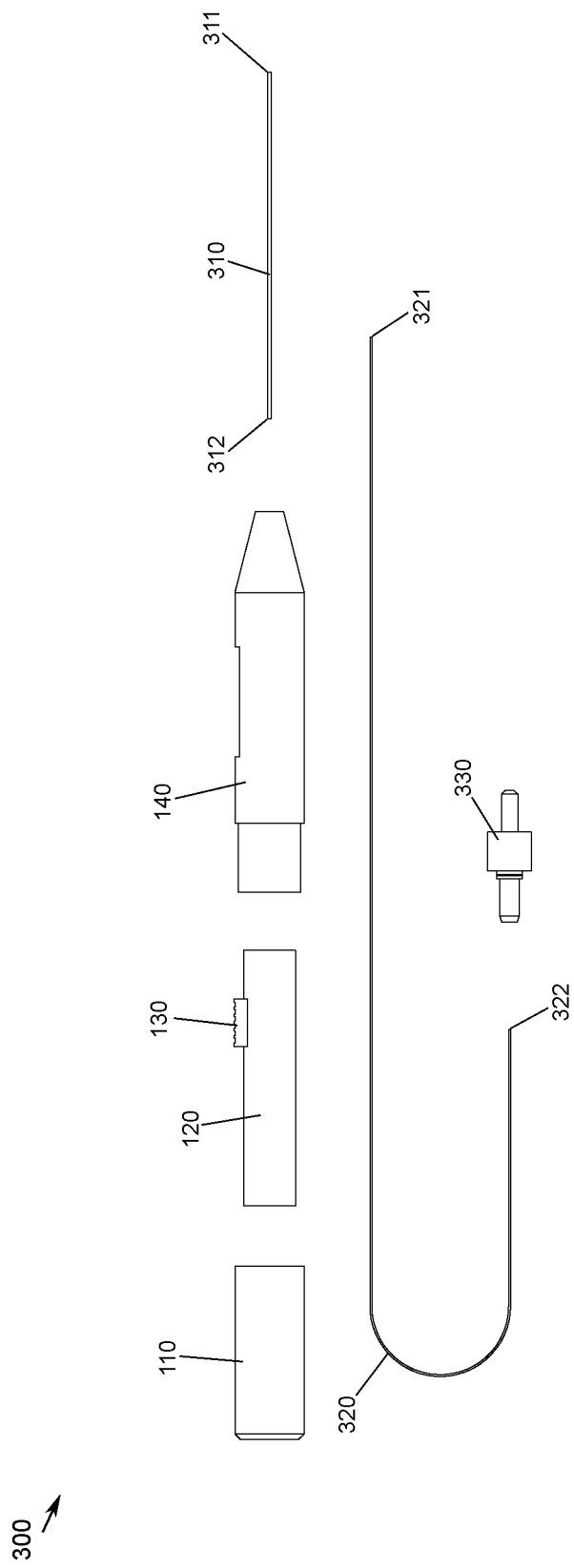
FIG. 3 is a schematic diagram illustrating an exploded view of a steerable laser probe assembly.

FIGS. 1A and 1B are schematic diagrams illustrating an exploded view of a handle assembly 100. FIG. 1A illustrates a side-view of a handle assembly 100. Illustratively, handle assembly 100 may comprise a handle end cap 110 having a handle end cap distal end 111 and a handle end cap proximal end 112, an actuation mechanism 120 having an actuation mechanism distal end 121 and an actuation mechanism proximal end 122, an actuation mechanism control 130 having an actuation mechanism control distal end 131 and an actuation mechanism control proximal end 132, and a handle base 140 having a handle base distal end 141 and a handle base proximal end 142. In one or more embodiments, handle base 140 may comprise a handle end cap interface 143 and an actuation mechanism control guide 145 having an actuation mechanism control guide distal end 146 and an actuation mechanism control guide proximal end 147.

FIG. 1B illustrates a cross-sectional view of a handle assembly 100. Illustratively, handle assembly 100 may comprise an actuation mechanism guide 150, a handle base interface 153, a handle base housing 155, an optic fiber housing 160, an inner bore 165, a flexible housing tube housing 170, a pressure mechanism housing 180, and a flexible housing tube guide 190. Handle end cap 110, actuation mechanism 120, actuation mechanism control 130, and handle base 140 may be manufactured from any suitable material, e.g., polymers, metals, metal alloys, etc., or from any combination of suitable materials.

FIGS. 2A and 2B are schematic diagrams illustrating a handle 200. FIG. 2A illustrates a side-view of a handle 200. Illustratively, handle 200 may comprise a handle distal end 201, a handle proximal end 202, a handle end cap 110, an actuation mechanism 120, an actuation mechanism control 130, and a handle base 140. In one or more embodiments, handle distal end 201 may comprise handle base distal end 141. Illustratively, handle proximal end 202 may comprise handle end cap proximal end 112. In one or more embodiments, actuation mechanism control 130 may be disposed within actuation mechanism control guide 145. Illustratively, actuation mechanism control 130 may be configured to control an actuation of actuation mechanism 120, e.g., an actuation of actuation mechanism 120 within actuation mechanism guide 150.

FIG. 2B illustrates a cross-sectional view of a handle 200. Illustratively, handle 200 may be assembled by disposing actuation mechanism 120 within actuation mechanism guide 150. In one or more embodiments, at least a portion of actuation mechanism guide 150 may be coated by a lubricant, e.g., Teflon, configured to facilitate an actuation of actuation mechanism 120 within actuation mechanism guide 150. Illustratively, a portion of handle end cap 110 may be adjacent to a portion of handle base 140, e.g., handle end cap distal end 111 may be adjacent to handle base proximal end 142. In one or more embodiments, a portion of handle base 140 may be disposed within handle end cap 110, e.g., handle base proximal end 142 may be disposed within handle base housing 155. Illustratively, a portion of handle base 140 may be disposed within handle end cap 110 wherein handle end cap interface 143 may be adjacent to handle base interface 153. In one or more embodiments, a portion of handle end cap 110 may be fixed to a portion of handle base 140, e.g., by an adhesive or any suitable fixation means. Illustratively, handle end cap 110 and handle base 140 may be manufactured as a single unit.

Illustratively, actuation mechanism 120 may be configured to actuate within actuation mechanism guide 150. In one or more embodiments, an actuation of actuation mechanism control 130 may be configured to actuate actuation mechanism 120 within actuation mechanism guide 150. Illustratively, an actuation of actuation mechanism control 130 towards actuation mechanism control guide distal end 146 and away from actuation mechanism control guide proximal end 147 may be configured to actuate actuation mechanism 120, e.g., towards handle distal end 201 and away from handle proximal end 202. In one or more embodiments, an actuation of actuation mechanism control 130 towards actuation mechanism control guide proximal end 147 and away from actuation mechanism control guide distal end 146 may be configured to actuate actuation mechanism 120, e.g., towards handle proximal end 202 and away from handle distal end 201.

FIG. 3 is a schematic diagram illustrating an exploded view of a steerable laser probe assembly 300. Illustratively, a steerable laser probe assembly 300 may comprise a handle end cap 110, an actuation mechanism 120, a handle base 140, a flexible housing tube 310 having a flexible housing tube distal end 311 and a flexible housing tube proximal end 312, an optic fiber 320 having an optic fiber distal end 321 and an optic fiber proximal end 322, and a light source interface 330. Illustratively, light source interface 330 may be configured to interface with optic fiber 320, e.g., at optic fiber proximal end 322. In one or more embodiments, light source interface 330 may comprise a standard light source connecter, e.g., an SMA connector.

Illustratively, a portion of flexible housing tube 310 may be fixed to actuation mechanism 120, e.g., flexible housing tube proximal end 312 may be fixed to actuation mechanism distal end 121. In one or more embodiments, a portion of flexible housing tube 310 may be fixed to actuation mechanism 120, e.g., by an adhesive or any suitable fixation means. Illustratively, a portion of flexible housing tube 310 may be disposed within actuation mechanism 120, e.g., flexible housing tube proximal end 312 may be disposed within flexible housing tube housing 170. In one or more embodiments, a portion of flexible housing tube 310 may be fixed within flexible housing tube housing 170, e.g., by an adhesive or any suitable fixation means. Illustratively, flexible housing tube 310 may be disposed within actuation mechanism guide 150 and flexible housing tube guide 190. In one or more embodiments, a portion of flexible housing tube 310 may extend from handle distal end 201, e.g., flexible housing tube distal end 311 may extend from handle distal end 201. Flexible housing tube 310 may be manufactured from any suitable material, e.g., polymers, metals, metal alloys, etc., or from any combination of suitable materials.

Illustratively, flexible housing tube 310 may comprise a shape memory material, e.g., Nitinol. In one or more embodiments, flexible housing tube 310 may be manufactured from a material having an ultimate tensile strength between 700 and 1000 MPa. Illustratively, flexible housing tube 310 may be manufactured from a material having ultimate tensile strength less than 700 MPa or greater than 1000 MPa. In one or more embodiments, flexible housing tube 310 may be manufactured from a material having a modulus of elasticity between 30 and 80 GPa. Illustratively, flexible housing tube 310 may be manufactured from a material having a modulus of elasticity less than 30 GPa or greater than 80 GPa.

In one or more embodiments, flexible housing tube 310 may be manufactured with dimensions suitable for performing microsurgical procedures, e.g., ophthalmic surgical procedures. Illustratively, flexible housing tube 310 may be manufactured at gauge sizes commonly used in ophthalmic surgical procedures, e.g., 23 gauge, 25 gauge, etc. In one or more embodiments, flexible housing tube 310 may be configured to be inserted in a cannula, e.g., a cannula used during an ophthalmic surgical procedure. For example, one or more properties of flexible housing tube 310 may be optimized to reduce friction as flexible housing tube 310 is inserted into a cannula. In one or more embodiments, one or more properties of flexible housing tube 310 may be optimized to reduce friction as flexible housing tube 310 is removed from a cannula. Illustratively, flexible housing tube 310 may have an ultimate tensile strength between 1000 MPa and 1100 MPa. In one or more embodiments, flexible housing tube 310 may have an ultimate tensile strength less than 1000 MPa or greater than 1100 MPa.

In one or more embodiments, optic fiber 320 may be disposed in optic fiber housing 160, actuation mechanism guide 150, inner bore 165, flexible housing tube housing 170, flexible housing tube 310, and flexible housing tube guide 190. Illustratively, optic fiber 320 may be disposed within flexible housing tube 310 wherein optic fiber distal end 321 may be adjacent to flexible housing tube distal end 311. In one or more embodiments, a portion of optic fiber 320 may be fixed to a portion of flexible housing tube 310, e.g., by an adhesive or any suitable fixation means. Illustratively, a portion of optic fiber 320 may be fixed in a position relative to handle base 140. In one or more embodiments, a portion of optic fiber 320 may be fixed within optic fiber housing 160, e.g., by an adhesive or any suitable fixation means. Illustratively, optic fiber 320 may be fixed in a position relative to handle base 140 and a portion of optic fiber 320 may be fixed to a portion of flexible housing tube 310.

In one or more embodiments, an actuation of actuation mechanism control 130 towards actuation mechanism control guide distal end 146 and away from actuation mechanism control guide proximal end 147 may be configured to extend actuation mechanism 120 relative to handle proximal end 202. Illustratively, an extension of actuation mechanism 120 relative to handle proximal end 202 may be configured to extend flexible housing tube housing 170 relative to handle proximal end 202. In one or more embodiments, an extension of flexible housing tube housing 170 relative to handle proximal end 202 may be configured to extend flexible housing tube 310 relative to handle proximal end 202. Illustratively, an extension of actuation mechanism control 130 relative to actuation mechanism control guide proximal end 147 may be configured to extend flexible housing tube 310 relative to handle proximal end 202. In one or more embodiments, an extension of flexible housing tube 310 relative to handle proximal end 202 may be configured to extend flexible housing tube 310 relative to optic fiber 320. Illustratively, a portion of optic fiber 320, e.g., a portion of optic fiber 320 fixed to flexible housing tube 310, may be configured to resist an extension of flexible housing tube 310 relative to optic fiber 320. In one or more embodiments, as flexible housing tube 310 is extended relative to optic fiber 320, e.g., due to an extension of actuation mechanism control 130 relative to actuation mechanism control guide proximal end 147, a portion of optic fiber 320 may be configured to apply a force to a portion of flexible housing tube 310. Illustratively, an application of a force to a portion of flexible housing tube 310 may be configured to cause flexible housing tube 310 to gradually curve, e.g., by compressing a portion of flexible housing tube 310. In one or more embodiments, a gradual curving of flexible housing tube 310 may be configured to gradually curve optic fiber 320. Illustratively, an extension of actuation mechanism control 130 relative to handle proximal end 202 may be configured to gradually curve optic fiber 320.

In one or more embodiments, an actuation of actuation mechanism control 130 towards actuation mechanism control guide proximal end 147 and away from actuation mechanism control guide distal end 146 may be configured to retract actuation mechanism 120 relative to handle proximal end 202. Illustratively, a retraction of actuation mechanism 120 relative to handle proximal end 202 may be configured to retract flexible housing tube housing 170 relative to handle proximal end 202. In one or more embodiments, a refraction of flexible housing tube housing 170 relative to handle proximal end 202 may be configured to retract flexible housing tube 310 relative to handle proximal end 202. Illustratively, a retraction of actuation mechanism control 130 relative to actuation mechanism control guide proximal end 147 may be configured to retract flexible housing tube 310 relative to handle proximal end 202. In one or more embodiments, a refraction of flexible housing tube 310 relative to handle proximal end 202 may be configured to retract flexible housing tube 310 relative to optic fiber 320. Illustratively, a portion of optic fiber 320, e.g., a portion of optic fiber 320 fixed to flexible housing tube 310, may be configured to facilitate a retraction of flexible housing tube 310 relative to optic fiber 320. In one or more embodiments, as flexible housing tube 310 is retracted relative to optic fiber 320, e.g., due to a refraction of actuation mechanism control 130 relative to actuation mechanism control guide proximal end 147, a portion of optic fiber 320 may be configured to reduce a force applied to a portion of flexible housing tube 310. Illustratively, a reduction of a force applied to a portion of flexible housing tube 310 may be configured to cause flexible housing tube 310 to gradually straighten, e.g., by decompressing a portion of flexible housing tube 310. In one or more embodiments, a gradual straightening of flexible housing tube 310 may be configured to gradually straighten optic fiber 320. Illustratively, a retraction of actuation mechanism control 130 relative to handle proximal end 202 may be configured to gradually straighten optic fiber 320.

Figure 4A:
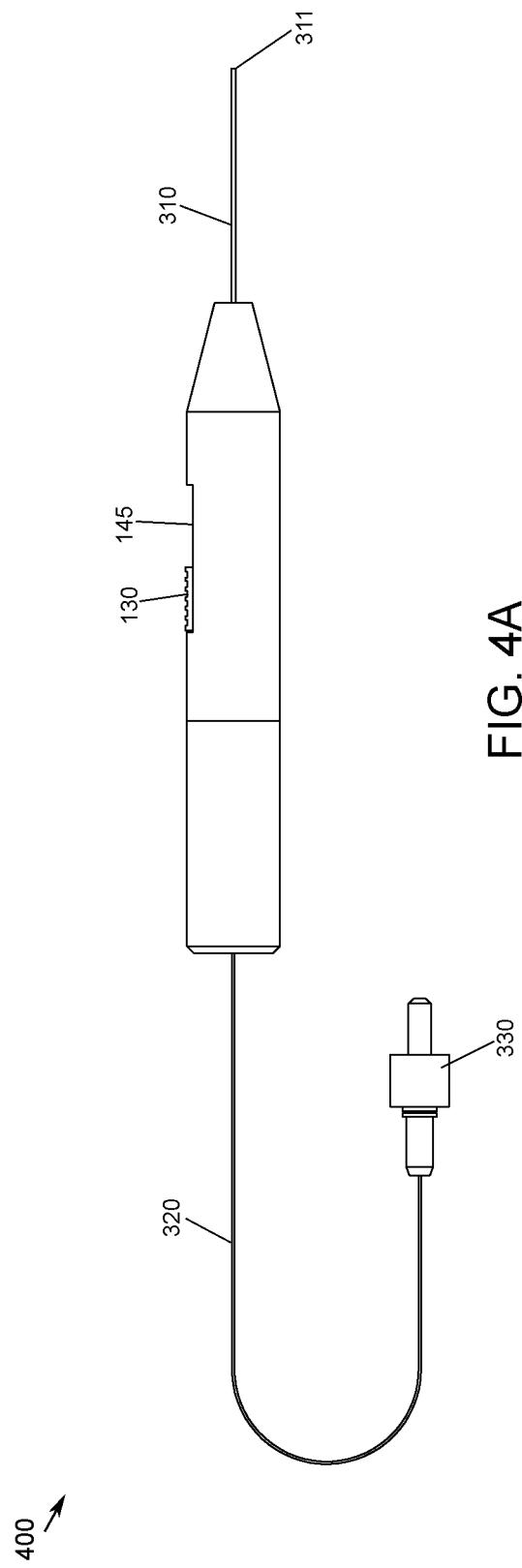

FIGS. 4A, 4B, 4C, 4D, and 4E illustrate a gradual curving of an optic fiber 320. FIG. 4A illustrates a straight optic fiber 400. In one or more embodiments, optic fiber 320 may comprise a straight optic fiber 400, e.g., when flexible housing tube 310 is fully refracted relative to handle proximal end 202. Illustratively, optic fiber 320 may comprise a straight optic fiber 400, e.g., when actuation mechanism control 130 is fully retracted relative to actuation mechanism control guide proximal end 147. In one or more embodiments, optic fiber 320 may comprise a straight optic fiber 400, e.g., when actuation mechanism 120 is fully retracted relative to handle proximal end 202. Illustratively, a line tangent to optic fiber distal end 321 may be parallel to a line tangent to flexible housing tube proximal end 312, e.g., when optic fiber 320 comprises a straight optic fiber 400.

Figure 4B:
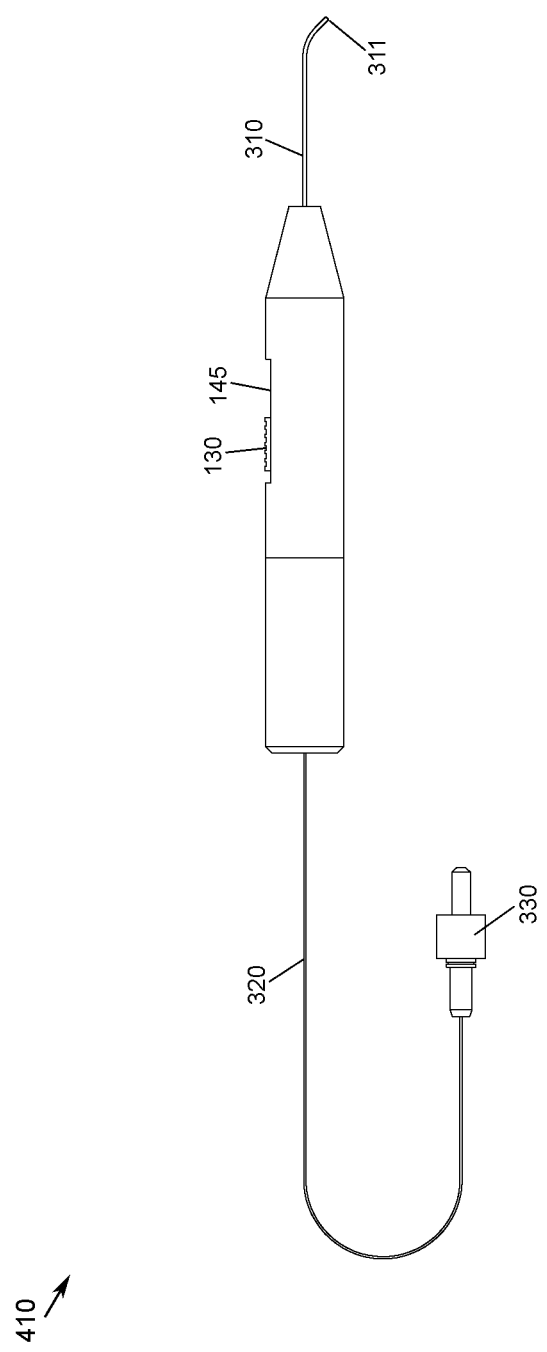

FIG. 4B illustrates an optic fiber in a first curved position 410. In one or more embodiments, an extension of actuation mechanism control 130 relative to handle proximal end 202 may be configured to gradually curve optic fiber 320 from a straight optic fiber 400 to an optic fiber in a first curved position 410. Illustratively, an extension of actuation mechanism control 130 relative to handle proximal end 202 may be configured to extend actuation mechanism 120 relative to handle proximal end 202. In one or more embodiments, an extension of actuation mechanism 120 relative to handle proximal end 202 may be configured to extend flexible housing tube 310 relative to optic fiber 320. Illustratively, an extension of flexible housing tube 310 relative to optic fiber 320 may be configured to apply a force to a portion of flexible housing tube 310. In one or more embodiments, an application of a force to a portion of flexible housing tube 310 may be configured to cause flexible housing tube 310 to gradually curve, e.g., by compressing a portion of flexible housing tube 310. Illustratively, a gradual curving of flexible housing tube 310 may be configured to gradually curve optic fiber 320, e.g., from a straight optic fiber 400 to an optic fiber in a first curved position 410. In one or more embodiments, a line tangent to optic fiber distal end 321 may intersect a line tangent to flexible housing tube proximal end 312 at a first angle, e.g., when optic fiber 320 comprises an optic fiber in a first curved position 410. Illustratively, the first angle may comprise any angle greater than zero degrees. For example, the first angle may comprise a 45 degree angle.

FIG. 4C illustrates an optic fiber in a second curved position 420. In one or more embodiments, an extension of actuation mechanism control 130 relative to handle proximal end 202 may be configured to gradually curve optic fiber 320 from an optic fiber in a first curved position 410 to an optic fiber in a second curved position 420. Illustratively, an extension of actuation mechanism control 130 relative to handle proximal end 202 may be configured to extend actuation mechanism 120 relative to handle proximal end 202. In one or more embodiments, an extension of actuation mechanism 120 relative to handle proximal end 202 may be configured to extend flexible housing tube 310 relative to optic fiber 320. Illustratively, an extension of flexible housing tube 310 relative to optic fiber 320 may be configured to apply a force to a portion of flexible housing tube 310. In one or more embodiments, an application of a force to a portion of flexible housing tube 310 may be configured to cause flexible housing tube 310 to gradually curve, e.g., by compressing a portion of flexible housing tube 310. Illustratively, a gradual curving of flexible housing tube 310 may be configured to gradually curve optic fiber 320, e.g., from an optic fiber in a first curved position 410 to an optic fiber in a second curved position 420. In one or more embodiments, a line tangent to optic fiber distal end 321 may intersect a line tangent to flexible housing tube proximal end 312 at a second angle, e.g., when optic fiber 320 comprises an optic fiber in a second curved position 420. Illustratively, the second angle may comprise any angle greater than the first angle. For example, the second angle may comprise a 90 degree angle.

Figure 4D:
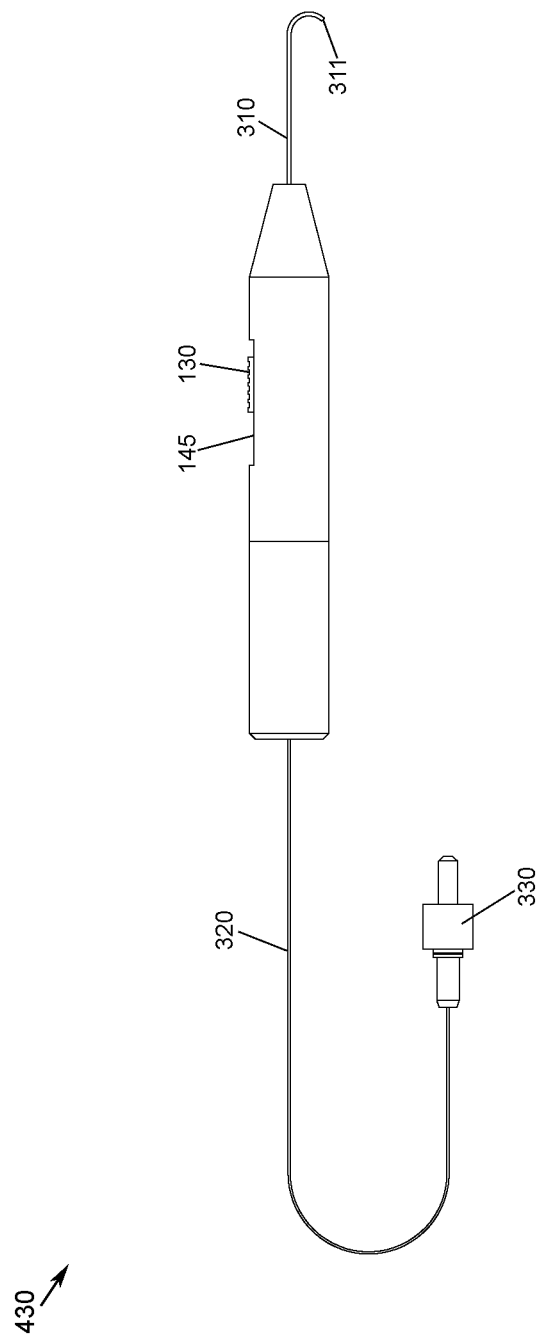

FIG. 4D illustrates an optic fiber in a third curved position 430. In one or more embodiments, an extension of actuation mechanism control 130 relative to handle proximal end 202 may be configured to gradually curve optic fiber 320 from an optic fiber in a second curved position 420 to an optic fiber in a third curved position 430. Illustratively, an extension of actuation mechanism control 130 relative to handle proximal end 202 may be configured to extend actuation mechanism 120 relative to handle proximal end 202. In one or more embodiments, an extension of actuation mechanism 120 relative to handle proximal end 202 may be configured to extend flexible housing tube 310 relative to optic fiber 320. Illustratively, an extension of flexible housing tube 310 relative to optic fiber 320 may be configured to apply a force to a portion of flexible housing tube 310. In one or more embodiments, an application of a force to a portion of flexible housing tube 310 may be configured to cause flexible housing tube 310 to gradually curve, e.g., by compressing a portion of flexible housing tube 310. Illustratively, a gradual curving of flexible housing tube 310 may be configured to gradually curve optic fiber 320, e.g., from an optic fiber in a second curved position 420 to an optic fiber in a third curved position 430. In one or more embodiments, a line tangent to optic fiber distal end 321 may intersect a line tangent to flexible housing tube proximal end 312 at a third angle, e.g., when optic fiber 320 comprises an optic fiber in a third curved position 430. Illustratively, the third angle may comprise any angle greater than the second angle. For example, the third angle may comprise a 135 degree angle.

Figure 4E:
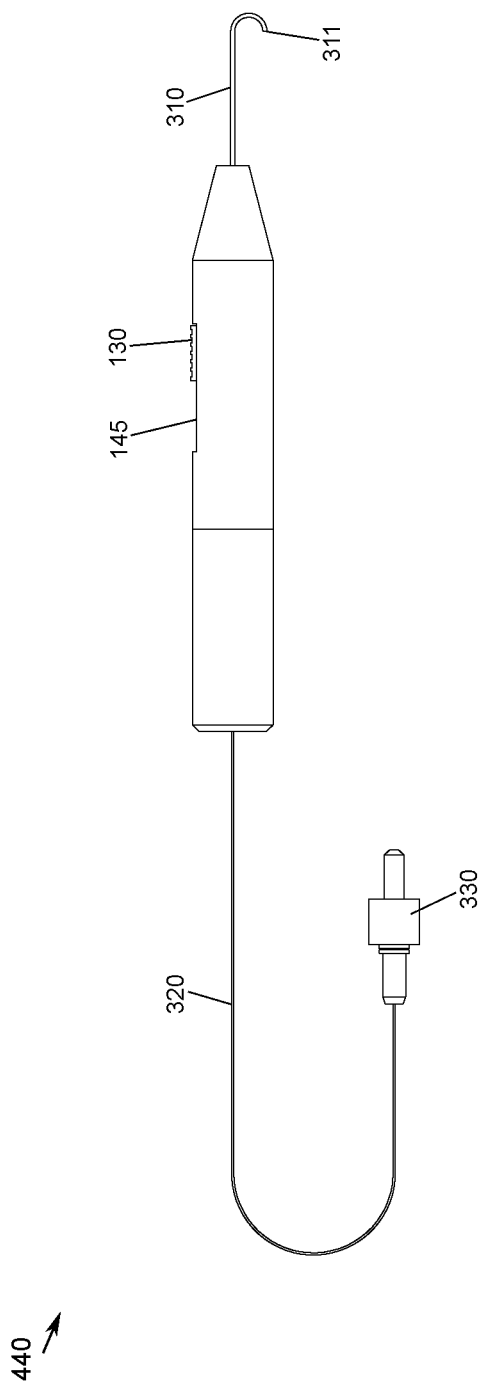

FIG. 4E illustrates an optic fiber in a fourth curved position 440. In one or more embodiments, an extension of actuation mechanism control 130 relative to handle proximal end 202 may be configured to gradually curve optic fiber 320 from an optic fiber in a third curved position 430 to an optic fiber in a fourth curved position 440. Illustratively, an extension of actuation mechanism control 130 relative to handle proximal end 202 may be configured to extend actuation mechanism 120 relative to handle proximal end 202. In one or more embodiments, an extension of actuation mechanism 120 relative to handle proximal end 202 may be configured to extend flexible housing tube 310 relative to optic fiber 320. Illustratively, an extension of flexible housing tube 310 relative to optic fiber 320 may be configured to apply a force to a portion of flexible housing tube 310. In one or more embodiments, an application of a force to a portion of flexible housing tube 310 may be configured to cause flexible housing tube 310 to gradually curve, e.g., by compressing a portion of flexible housing tube 310. Illustratively, a gradual curving of flexible housing tube 310 may be configured to gradually curve optic fiber 320, e.g., from an optic fiber in a third curved position 430 to an optic fiber in a fourth curved position 440. In one or more embodiments, a line tangent to optic fiber distal end 321 may be parallel to a line tangent to flexible housing tube proximal end 312, e.g., when optic fiber 320 comprises an optic fiber in a fourth curved position 440.

In one or more embodiments, one or more properties of a steerable laser probe may be adjusted to attain one or more desired steerable laser probe features. For example, a length that flexible housing tube distal end 311 extends from actuation mechanism distal end 121 may be adjusted to vary an amount of extension of actuation mechanism control 130 relative to handle proximal end 202 configured to curve flexible housing tube 310 to a particular curved position. In one or more embodiments, a stiffness of flexible housing tube 310 may be adjusted to vary an amount of extension of actuation mechanism control 130 relative to handle proximal end 202 configured to curve flexible housing tube 310 to a particular curved position. Illustratively, flexible housing tube 310 may comprise a solid tube structure. In one or more embodiments, flexible housing tube 310 may comprise one or more apertures, e.g., configured to vary a stiffness of flexible housing tube 310. Illustratively, a material comprising flexible housing tube 310 may be adjusted to vary an amount of extension of actuation mechanism control 130 relative to handle proximal end 202 configured to curve flexible housing tube 310 to a particular curved position. In one or more embodiments, a stiffness of flexible housing tube 310 may be adjusted to vary a bend radius of flexible housing tube 310. For example, a stiffness of flexible housing tube 310 may be adjusted to vary a radius of curvature of flexible housing tube 310, e.g., when flexible housing tube 310 is in a particular curved position.

In one or more embodiments, a geometry of actuation mechanism 120 may be adjusted to vary an amount of extension of actuation mechanism control 130 relative to handle proximal end 202 configured to curve flexible housing tube 310 to a particular curved position. Illustratively, a geometry of actuation mechanism guide 150 may be adjusted to vary an amount of extension of actuation mechanism control 130 relative to handle proximal end 202 configured to curve flexible housing tube 310 to a particular curved position. In one or more embodiments, a geometry of handle end cap 110 or a geometry of handle base 140 may be adjusted to vary an amount of extension of actuation mechanism control 130 relative to handle proximal end 202 configured to curve flexible housing tube 310 to a particular curved position. Illustratively, one or more locations within flexible housing tube 310 wherein optic fiber 320 may be fixed to a portion of flexible housing tube 310 may be adjusted to vary an amount of extension of actuation mechanism control 130 relative to handle proximal end 202 configured to curve flexible housing tube 310 to a particular curved position.

In one or more embodiments, at least a portion of optic fiber 320 may be enclosed in an optic fiber sleeve configured to, e.g., protect optic fiber 320, vary a stiffness of optic fiber 320, vary an optical property of optic fiber 320, etc. Illustratively, an optic fiber sleeve may be configured to compress a portion of flexible housing tube 310. For example, an optic fiber sleeve may enclose a portion of optic fiber 320 and the optic fiber sleeve may be fixed in a position relative to handle base 140, e.g., the optic fiber sleeve may be fixed within optic fiber housing 160 by an adhesive or any suitable fixation means. Illustratively, a portion of the optic fiber sleeve may be fixed to a portion of flexible housing tube 310, e.g., by an adhesive or any suitable fixation means. In one or more embodiments, an extension of actuation mechanism control 130 relative to handle proximal end 202 may be configured to extend flexible housing tube 310 relative to an optic fiber sleeve. Illustratively, an extension of flexible housing tube 310 relative to an optic fiber sleeve may be configured to cause the optic fiber sleeve to apply a force, e.g., a compressive force, to a portion of flexible housing tube 310 causing flexible housing tube 310 to gradually curve. In one or more embodiments, a gradual curving of flexible housing tube 310 may be configured to gradually curve optic fiber 320.

Illustratively, optic fiber 320 may comprise a buffer, a cladding disposed in the buffer, and a core disposed in the cladding. In one or more embodiments, at least a portion of optic fiber 320 may comprise a buffer configured to protect an optical property of optic fiber 320. Illustratively, at least a portion of optic fiber 320 may comprise a buffer configured to protect an optical layer of optic fiber 320, e.g., the buffer may protect an optical layer of a curved portion of optic fiber 320. In one or more embodiments, at least a portion of optic fiber 320 may comprise a polyimide buffer configured to protect an optical property of optic fiber 320. For example, at least a portion of optic fiber 320 may comprise a Kapton buffer configured to protect an optical property of optic fiber 320.

Illustratively, a steerable laser probe may be configured to indicate, e.g., to a surgeon, a direction that optic fiber 320 may curve, e.g., due to an extension of actuation mechanism control 130 relative to handle proximal end 202. In one or more embodiments, a portion of a steerable laser probe, e.g., handle 200, may be marked in a manner configured to indicate a direction that optic fiber 320 may curve. For example, a portion of flexible housing tube 310 may comprise a mark configured to indicate a direction that optic fiber 320 may curve. Illustratively, flexible housing tube 310 may comprise a slight curve, e.g., a curve less than 7.5 degrees, when actuation mechanism control 130 is fully refracted relative to handle proximal end 202. In one or more embodiments, flexible housing tube 310 may comprise a slight curve configured to indicate a direction that optic fiber 320 may curve, e.g., due to an extension of actuation mechanism control 130 relative to handle proximal end 202.

Illustratively, handle base 140 may comprise a plurality of actuation mechanism control guides 145. In one or more embodiments, actuation mechanism 120 may comprise a plurality of actuation mechanism controls 130. For example, handle 200 may comprise a first actuation mechanism control 130 disposed within a first actuation mechanism control guide 145 and a second actuation mechanism control 130 disposed in a second actuation mechanism control guide 145. Illustratively, an extension of either the first actuation mechanism control 130 or the second actuation mechanism control 130 relative to handle proximal end 202 may be configured to extend actuation mechanism 120 relative to handle proximal end 202. In one or more embodiments, a retraction of either the first actuation mechanism control 130 or the second actuation mechanism control 130 relative to handle proximal end 202 may be configured to retract actuation mechanism 120 relative to handle proximal end 202. Illustratively, handle 200 may comprise a third actuation mechanism control 130 disposed in a third actuation mechanism control guide 145. In one or more embodiments, an extension of either the first actuation mechanism control 130, the second actuation mechanism control 130, or the third actuation mechanism control 130 relative to handle proximal end 202 may be configured to extend actuation mechanism 120 relative to handle proximal end 202. Illustratively, a retraction of either the first actuation mechanism control 130, the second actuation mechanism control 130, or the third actuation mechanism control 130 relative to handle proximal end 202 may be configured to retract actuation mechanism 120 relative to handle proximal end 202.

In one or more embodiments, a steerable laser probe may comprise a pressure mechanism configured to provide a force. Illustratively, a pressure mechanism may be disposed within pressure mechanism housing 180. In one or more embodiments, a pressure mechanism may be configured to provide a constant force. Illustratively, a pressure mechanism may be configured to provide a variable force. In one or more embodiments, a pressure mechanism may be configured to provide a resistive force, e.g., to resist an extension of actuation mechanism 120 relative to handle proximal end 202. Illustratively, a pressure mechanism may be configured to provide a facilitating force, e.g., to facilitate a retraction of actuation mechanism 120 relative to handle proximal end 202. In one or more embodiments, a pressure mechanism may comprise a spring or a coil. Illustratively, a pressure mechanism may comprise a pneumatic system or any system configured to provide a force.

Figure 5A:
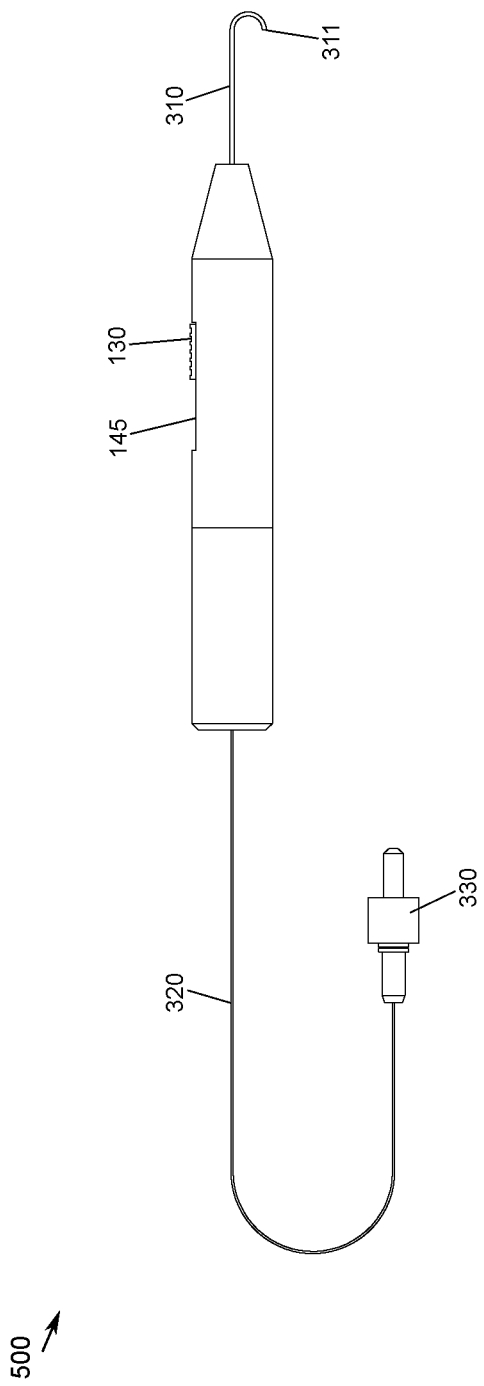
FIGS. 5A, 5B, 5C, 5D, and 5E are schematic diagrams illustrating a gradual straightening of an optic fiber.

FIGS. 5A, 5B, 5C, 5D, and 5E illustrate a gradual straightening of an optic fiber 320. FIG. 5A illustrates a fully curved optic fiber 500. In one or more embodiments, optic fiber 320 may comprise a fully curved optic fiber 500, e.g., when flexible housing tube 310 is fully extended relative to handle proximal end 202. Illustratively, optic fiber 320 may comprise a fully curved optic fiber 500, e.g., when actuation mechanism control 130 is fully extended relative to actuation mechanism control guide proximal end 147. In one or more embodiments, optic fiber 320 may comprise a fully curved optic fiber 500, e.g., when actuation mechanism 120 is fully extended relative to handle proximal end 202. Illustratively, a line tangent to optic fiber distal end 321 may be parallel to a line tangent to flexible housing tube proximal end 312, e.g., when optic fiber 320 comprises a fully curved optic fiber 500.

Figure 5B:
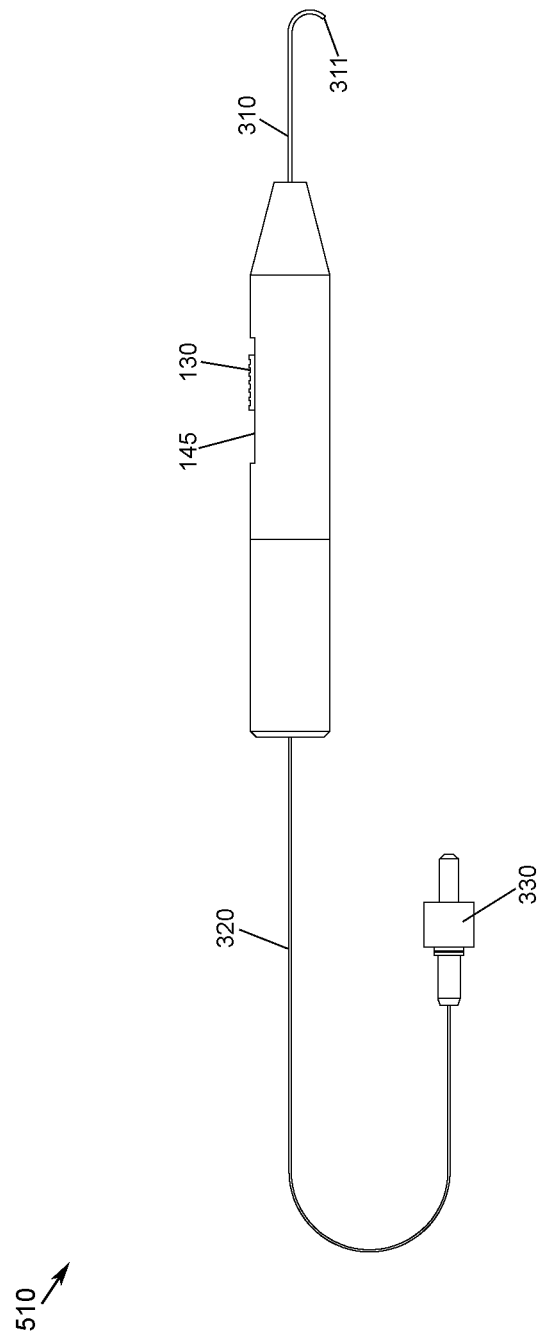

FIG. 5B illustrates an optic fiber in a first partially straightened position 510. In one or more embodiments, a retraction of actuation mechanism control 130 relative to handle proximal end 202 may be configured to gradually straighten optic fiber 320 from a fully curved optic fiber 500 to an optic fiber in a first partially straightened position 510. Illustratively, a retraction of actuation mechanism control 130 relative to handle proximal end 202 may be configured to retract actuation mechanism 120 relative to handle proximal end 202. In one or more embodiments, a retraction of actuation mechanism 120 relative to handle proximal end 202 may be configured to retract flexible housing tube 310 relative to optic fiber 320. Illustratively, a retraction of flexible housing tube 310 relative to optic fiber 320 may be configured to reduce a force applied to a portion of flexible housing tube 310. In one or more embodiments, a reduction of a force applied to a portion of flexible housing tube 310 may be configured to cause flexible housing tube 310 to gradually straighten, e.g., by decompressing a portion of flexible housing tube 310. Illustratively, a gradual straightening of flexible housing tube 310 may be configured to gradually straighten optic fiber 320, e.g., from a fully curved optic fiber 500 to an optic fiber in a first partially straightened position 510. In one or more embodiments, a line tangent to optic fiber distal end 321 may intersect a line tangent to flexible housing tube proximal end 312 at a first partially straightened angle, e.g., when optic fiber 320 comprises an optic fiber in a first partially straightened position 510. Illustratively, the first partially straightened angle may comprise any angle less than 180 degrees. For example, the first partially straightened angle may comprise a 135 degree angle.

Figure 5C:
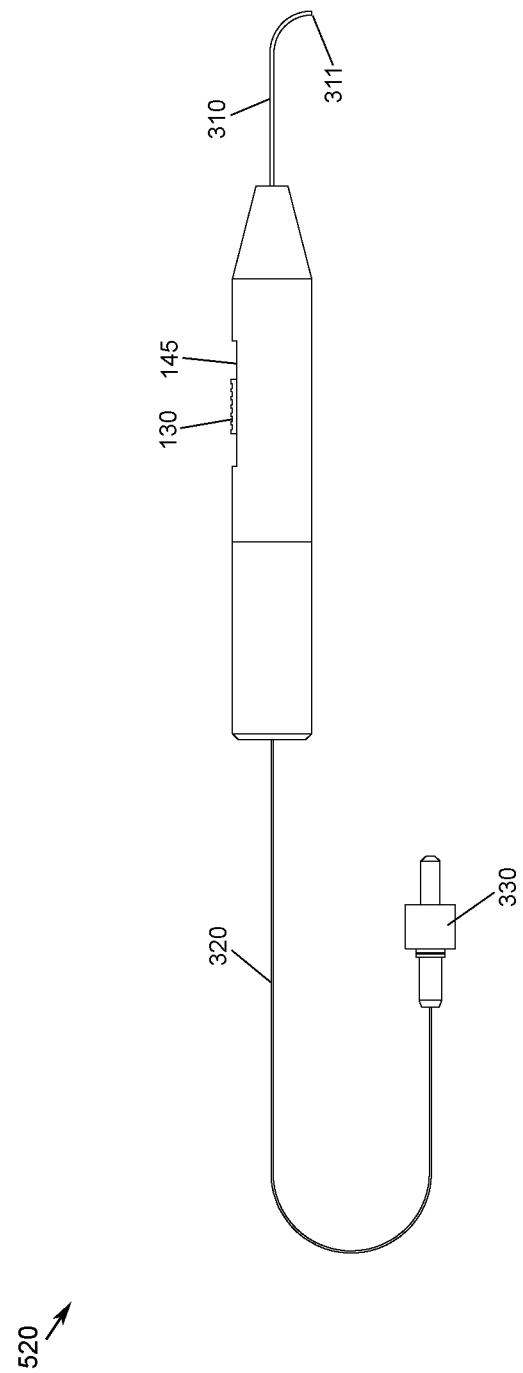

FIG. 5C illustrates an optic fiber in a second partially straightened position 520. In one or more embodiments, a retraction of actuation mechanism control 130 relative to handle proximal end 202 may be configured to gradually straighten optic fiber 320 from an optic fiber in a first partially straightened position 510 to an optic fiber in a second partially straightened position 520. Illustratively, a retraction of actuation mechanism control 130 relative to handle proximal end 202 may be configured to retract actuation mechanism 120 relative to handle proximal end 202. In one or more embodiments, a retraction of actuation mechanism 120 relative to handle proximal end 202 may be configured to retract flexible housing tube 310 relative to optic fiber 320. Illustratively, a retraction of flexible housing tube 310 relative to optic fiber 320 may be configured to reduce a force applied to a portion of flexible housing tube 310. In one or more embodiments, a reduction of a force applied to a portion of flexible housing tube 310 may be configured to cause flexible housing tube 310 to gradually straighten, e.g., by decompressing a portion of flexible housing tube 310. Illustratively, a gradual straightening of flexible housing tube 310 may be configured to gradually straighten optic fiber 320, e.g., from an optic fiber in a first partially straightened position 510 to an optic fiber in a second partially straightened position 520. In one or more embodiments, a line tangent to optic fiber distal end 321 may intersect a line tangent to flexible housing tube proximal end 312 at a second partially straightened angle, e.g., when optic fiber 320 comprises an optic fiber in a second partially straightened position 520. Illustratively, the second partially straightened angle may comprise any angle less than the first partially straightened angle. For example, the second partially straightened angle may comprise a 90 degree angle.

Figure 5D:
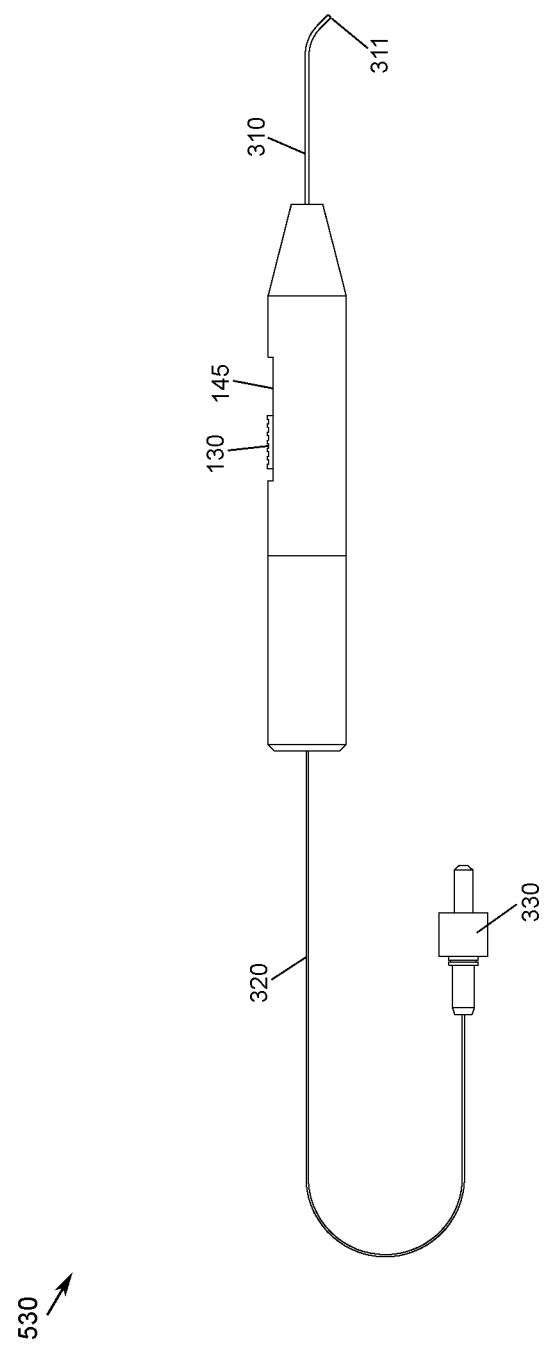

FIG. 5D illustrates an optic fiber in a third partially straightened position 530. In one or more embodiments, a retraction of actuation mechanism control 130 relative to handle proximal end 202 may be configured to gradually straighten optic fiber 320 from an optic fiber in a second partially straightened position 520 to an optic fiber in a third partially straightened position 530. Illustratively, a retraction of actuation mechanism control 130 relative to handle proximal end 202 may be configured to retract actuation mechanism 120 relative to handle proximal end 202. In one or more embodiments, a retraction of actuation mechanism 120 relative to handle proximal end 202 may be configured to retract flexible housing tube 310 relative to optic fiber 320. Illustratively, a retraction of flexible housing tube 310 relative to optic fiber 320 may be configured to reduce a force applied to a portion of flexible housing tube 310. In one or more embodiments, a reduction of a force applied to a portion of flexible housing tube 310 may be configured to cause flexible housing tube 310 to gradually straighten, e.g., by decompressing a portion of flexible housing tube 310. Illustratively, a gradual straightening of flexible housing tube 310 may be configured to gradually straighten optic fiber 320, e.g., from an optic fiber in a second partially straightened position 520 to an optic fiber in a third partially straightened position 530. In one or more embodiments, a line tangent to optic fiber distal end 321 may intersect a line tangent to flexible housing tube proximal end 312 at a third partially straightened angle, e.g., when optic fiber 320 comprises an optic fiber in a third partially straightened position 530. Illustratively, the third partially straightened angle may comprise any angle less than the second partially straightened angle. For example, the third partially straightened angle may comprise a 45 degree angle.

Figure 5E:
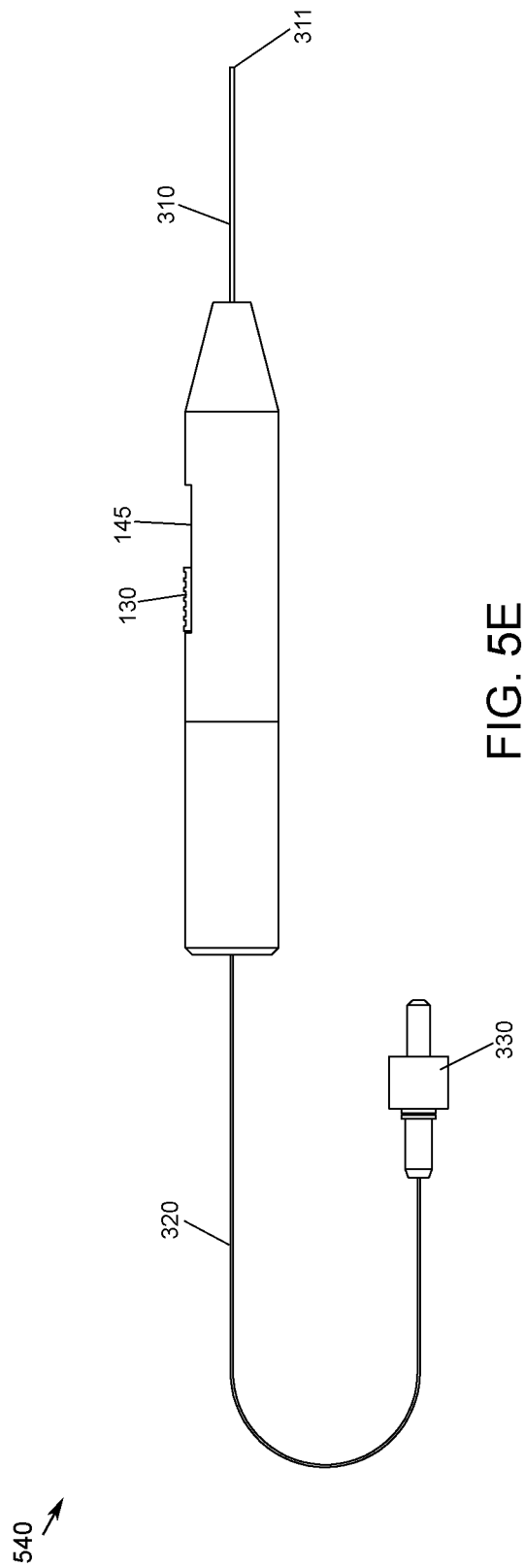

FIG. 5E illustrates an optic fiber in a fully straightened position 540. In one or more embodiments, a retraction of actuation mechanism control 130 relative to handle proximal end 202 may be configured to gradually straighten optic fiber 320 from an optic fiber in a third partially straightened position 530 to an optic fiber in a fully straightened position 540. Illustratively, a retraction of actuation mechanism control 130 relative to handle proximal end 202 may be configured to retract actuation mechanism 120 relative to handle proximal end 202. In one or more embodiments, a retraction of actuation mechanism 120 relative to handle proximal end 202 may be configured to retract flexible housing tube 310 relative to optic fiber 320. Illustratively, a retraction of flexible housing tube 310 relative to optic fiber 320 may be configured to reduce a force applied to a portion of flexible housing tube 310. In one or more embodiments, a reduction of a force applied to a portion of flexible housing tube 310 may be configured to cause flexible housing tube 310 to gradually straighten, e.g., by decompressing a portion of flexible housing tube 310. Illustratively, a gradual straightening of flexible housing tube 310 may be configured to gradually straighten optic fiber 320, e.g., from an optic fiber in a third partially straightened position 530 to an optic fiber in a fully straightened position 540. In one or more embodiments, a line tangent to optic fiber distal end 321 may be parallel to a line tangent to flexible housing tube proximal end 312, e.g., when optic fiber 320 comprises an optic fiber in a fully straightened position 540.

Illustratively, a surgeon may aim optic fiber distal end 321 at any of a plurality of targets within an eye, e.g., to perform a photocoagulation procedure, to illuminate a surgical target site, etc. In one or more embodiments, a surgeon may aim optic fiber distal end 321 at any target within a particular transverse plane of the inner eye by, e.g., rotating handle 200 to orient flexible housing tube 310 in an orientation configured to cause a curvature of flexible housing tube 310 within the particular transverse plane of the inner eye and varying an amount of extension of actuation mechanism control 130 relative to handle proximal end 202. Illustratively, a surgeon may aim optic fiber distal end 321 at any target within a particular sagittal plane of the inner eye by, e.g., rotating handle 200 to orient flexible housing tube 310 in an orientation configured to cause a curvature of flexible housing tube 310 within the particular sagittal plane of the inner eye and varying an amount of extension of actuation mechanism control 130 relative to handle proximal end 202. In one or more embodiments, a surgeon may aim optic fiber distal end 321 at any target within a particular frontal plane of the inner eye by, e.g., varying an amount of extension of actuation mechanism control 130 relative to handle proximal end 202 to orient a line tangent to optic fiber distal end 321 wherein the line tangent to optic fiber distal end 321 is within the particular frontal plane of the inner eye and rotating handle 200. Illustratively, a surgeon may aim optic fiber distal end 321 at any target located outside of the particular transverse plane, the particular sagittal plane, and the particular frontal plane of the inner eye, e.g., by varying a rotational orientation of handle 200 and varying an amount of extension of actuation mechanism control 130 relative to handle proximal end 202. In one or more embodiments, a surgeon may aim optic fiber distal end 321 at any target of a plurality of targets within an eye, e.g., without increasing a length of a portion of a steerable laser probe within the eye. Illustratively, a surgeon may aim optic fiber distal end 321 at any target of a plurality of targets within an eye, e.g., without decreasing a length of a portion of a steerable laser probe within the eye.

FIGS. 6A and 6B are schematic diagrams illustrating an exploded view of a handle assembly 600. FIG. 6A illustrates a side-view of a handle assembly 600. Illustratively, handle assembly 600 may comprise a handle end cap 610 having a handle end cap distal end 611 and a handle end cap proximal end 612, an actuation mechanism 620 having an actuation mechanism distal end 621 and an actuation mechanism proximal end 622, an actuation mechanism control 630 having an actuation mechanism control distal end 631 and an actuation mechanism control proximal end 632, and a handle base 640 having a handle base distal end 641 and a handle base proximal end 642. In one or more embodiments, handle base 640 may comprise a handle end cap interface 643 and an actuation mechanism control guide 645 having an actuation mechanism control guide distal end 646 and an actuation mechanism control guide proximal end 647.

FIG. 6B illustrates a cross-sectional view of a handle assembly 600. Illustratively, handle assembly 600 may comprise an actuation mechanism guide 650, a handle base interface 653, a handle base housing 655, a wire housing 660, an inner bore 665, a flexible housing tube housing 670, a pressure mechanism housing 680, and a flexible housing tube guide 690. Handle end cap 610, actuation mechanism 620, actuation mechanism control 630, and handle base 640 may be manufactured from any suitable material, e.g., polymers, metals, metal alloys, etc., or from any combination of suitable materials.

FIGS. 7A and 7B are schematic diagrams illustrating a handle 700. FIG. 7A illustrates a side-view of a handle 700. Illustratively, handle 700 may comprise a handle distal end 701, a handle proximal end 702, a handle end cap 610, an actuation mechanism 620, an actuation mechanism control 630, and a handle base 640. In one or more embodiments, handle distal end 701 may comprise handle base distal end 641. Illustratively, handle proximal end 702 may comprise handle end cap proximal end 612. In one or more embodiments, actuation mechanism control 630 may be disposed within actuation mechanism control guide 645. Illustratively, actuation mechanism control 630 may be configured to control an actuation of actuation mechanism 620, e.g., an actuation of actuation mechanism 620 within actuation mechanism guide 650.

FIG. 7B illustrates a cross-sectional view of a handle 700. Illustratively, handle 700 may be assembled by disposing actuation mechanism 620 within actuation mechanism guide 650. In one or more embodiments, at least a portion of actuation mechanism guide 650 may be coated by a lubricant, e.g., Teflon, configured to facilitate an actuation of actuation mechanism 620 within actuation mechanism guide 650. Illustratively, a portion of handle end cap 610 may be adjacent to a portion of handle base 640, e.g., handle end cap distal end 611 may be adjacent to handle base proximal end 642. In one or more embodiments, a portion of handle base 640 may be disposed within handle end cap 610, e.g., handle base proximal end 642 may be disposed within handle base housing 655. Illustratively, a portion of handle base 640 may be disposed within handle end cap 610 wherein handle end cap interface 643 may be adjacent to handle base interface 653. In one or more embodiments, a portion of handle end cap 610 may be fixed to a portion of handle base 640, e.g., by an adhesive or any suitable fixation means. Illustratively, handle end cap 610 and handle base 640 may be manufactured as a single unit.

Illustratively, actuation mechanism 620 may be configured to actuate within actuation mechanism guide 650. In one or more embodiments, an actuation of actuation mechanism control 630 may be configured to actuate actuation mechanism 620 within actuation mechanism guide 650. Illustratively, an actuation of actuation mechanism control 630 towards actuation mechanism control guide distal end 646 and away from actuation mechanism control guide proximal end 647 may be configured to actuate actuation mechanism 620, e.g., towards handle distal end 701 and away from handle proximal end 702. In one or more embodiments, an actuation of actuation mechanism control 630 towards actuation mechanism control guide proximal end 647 and away from actuation mechanism control guide distal end 646 may be configured to actuate actuation mechanism 620, e.g., towards handle proximal end 702 and away from handle distal end 701.

Figure 8:
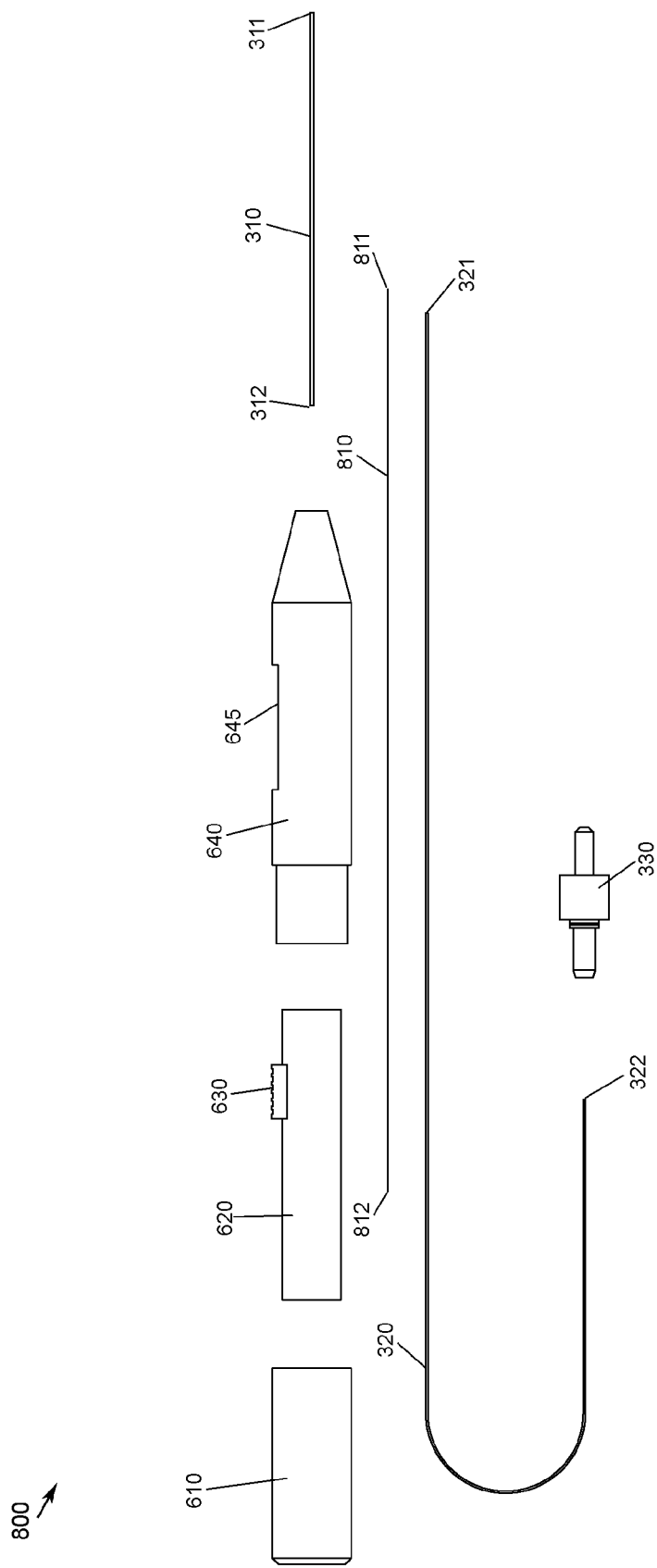
FIG. 8 is a schematic diagram illustrating an exploded view of a steerable laser probe assembly.

FIG. 8 is a schematic diagram illustrating an exploded view of a steerable laser probe assembly 800. Illustratively, a steerable laser probe assembly 800 may comprise a handle end cap 610, an actuation mechanism 620, a handle base 640, a flexible housing tube 310 having a flexible housing tube distal end 311 and a flexible housing tube proximal end 312, an optic fiber 320 having an optic fiber distal end 321 and an optic fiber proximal end 322, a wire 810 having a wire distal end 811 and a wire proximal end 812, and a light source interface 330. Illustratively, light source interface 330 may be configured to interface with optic fiber 320, e.g., at optic fiber proximal end 322. In one or more embodiments, light source interface 330 may comprise a standard light source connecter, e.g., an SMA connector.

Illustratively, a portion of flexible housing tube 310 may be fixed to actuation mechanism 620, e.g., flexible housing tube proximal end 312 may be fixed to actuation mechanism distal end 621. In one or more embodiments, a portion of flexible housing tube 310 may be fixed to actuation mechanism 620, e.g., by an adhesive or any suitable fixation means. Illustratively, a portion of flexible housing tube 310 may be disposed within actuation mechanism 620, e.g., flexible housing tube proximal end 312 may be disposed within flexible housing tube housing 670. In one or more embodiments, a portion of flexible housing tube 310 may be fixed within flexible housing tube housing 670, e.g., by an adhesive or any suitable fixation means. Illustratively, flexible housing tube 310 may be disposed within actuation mechanism guide 650 and flexible housing tube guide 690. In one or more embodiments, a portion of flexible housing tube 310 may extend from handle distal end 701, e.g., flexible housing tube distal end 311 may extend from handle distal end 701. Flexible housing tube 310 may be manufactured from any suitable material, e.g., polymers, metals, metal alloys, etc., or from any combination of suitable materials.

Illustratively, flexible housing tube 310 may comprise a shape memory material, e.g., Nitinol. In one or more embodiments, flexible housing tube 310 may be manufactured from a material having an ultimate tensile strength between 700 and 1000 MPa. Illustratively, flexible housing tube 310 may be manufactured from a material having ultimate tensile strength less than 700 MPa or greater than 1000 MPa. In one or more embodiments, flexible housing tube 310 may be manufactured from a material having a modulus of elasticity between 30 and 80 GPa. Illustratively, flexible housing tube 310 may be manufactured from a material having a modulus of elasticity less than 30 GPa or greater than 80 GPa.

In one or more embodiments, flexible housing tube 310 may be manufactured with dimensions suitable for performing microsurgical procedures, e.g., ophthalmic surgical procedures. Illustratively, flexible housing tube 310 may be manufactured at gauge sizes commonly used in ophthalmic surgical procedures, e.g., 23 gauge, 25 gauge, etc. In one or more embodiments, flexible housing tube 310 may be configured to be inserted in a cannula, e.g., a cannula used during an ophthalmic surgical procedure. For example, one or more properties of flexible housing tube 310 may be optimized to reduce friction as flexible housing tube 310 is inserted into a cannula. In one or more embodiments, one or more properties of flexible housing tube 310 may be optimized to reduce friction as flexible housing tube 310 is removed from a cannula. Illustratively, flexible housing tube 310 may have an ultimate tensile strength between 1000 MPa and 1100 MPa. In one or more embodiments, flexible housing tube 310 may have an ultimate tensile strength less than 1000 MPa or greater than 1100 MPa.

In one or more embodiments, optic fiber 320 may be disposed in wire housing 660, actuation mechanism guide 650, inner bore 665, flexible housing tube housing 670, flexible housing tube 310, and flexible housing tube guide 690. Illustratively, optic fiber 320 may be disposed within flexible housing tube 310 wherein optic fiber distal end 321 may be adjacent to flexible housing tube distal end 311. In one or more embodiments, a portion of optic fiber 320 may be fixed to a portion of flexible housing tube 310, e.g., by an adhesive or any suitable fixation means.

Illustratively, wire 810 may be disposed within wire housing 660, actuation mechanism guide 650, inner bore 665, flexible housing tube housing 670, flexible housing tube 310, and flexible housing tube guide 690. In one or more embodiments, wire 810 may be disposed within flexible housing tube 310 wherein wire distal end 811 may be adjacent to flexible housing tube distal end 311. Illustratively, a portion of wire 810 may be fixed to a portion of flexible housing tube 310, e.g., by an adhesive or any suitable fixation means. In one or more embodiments, wire 810 may be fixed in a position relative to handle base 640. Illustratively, wire 810 may be fixed within wire housing 660, e.g., by an adhesive or any other suitable fixation means. In one or more embodiments, wire 810 may be fixed in a position relative to handle base 640 and a portion of wire 810 may be fixed to a portion of flexible housing tube 310.

In one or more embodiments, an actuation of actuation mechanism control 630 towards actuation mechanism control guide distal end 646 and away from actuation mechanism control guide proximal end 647 may be configured to extend actuation mechanism 620 relative to handle proximal end 702. Illustratively, an extension of actuation mechanism 620 relative to handle proximal end 702 may be configured to extend flexible housing tube housing 670 relative to handle proximal end 702. In one or more embodiments, an extension of flexible housing tube housing 670 relative to handle proximal end 702 may be configured to extend flexible housing tube 310 relative to handle proximal end 702. Illustratively, an extension of actuation mechanism control 630 relative to actuation mechanism control guide proximal end 647 may be configured to extend flexible housing tube 310 relative to handle proximal end 702. In one or more embodiments, an extension of flexible housing tube 310 relative to handle proximal end 702 may be configured to extend flexible housing tube 310 relative to wire 810. Illustratively, a portion of wire 810, e.g., a portion of wire 810 fixed to flexible housing tube 310, may be configured to resist an extension of flexible housing tube 310 relative to wire 810. In one or more embodiments, as flexible housing tube 310 is extended relative to wire 810, e.g., due to an extension of actuation mechanism control 630 relative to actuation mechanism control guide proximal end 647, a portion of wire 810 may be configured to apply a force to a portion of flexible housing tube 310. Illustratively, an application of a force to a portion of flexible housing tube 310 may be configured to cause flexible housing tube 310 to gradually curve, e.g., by compressing a portion of flexible housing tube 310. In one or more embodiments, a gradual curving of flexible housing tube 310 may be configured to gradually curve optic fiber 320. Illustratively, an extension of actuation mechanism control 630 relative to handle proximal end 702 may be configured to gradually curve optic fiber 320.

In one or more embodiments, an actuation of actuation mechanism control 630 towards actuation mechanism control guide proximal end 647 and away from actuation mechanism control guide distal end 646 may be configured to retract actuation mechanism 620 relative to handle proximal end 702. Illustratively, a retraction of actuation mechanism 620 relative to handle proximal end 702 may be configured to retract flexible housing tube housing 670 relative to handle proximal end 702. In one or more embodiments, a refraction of flexible housing tube housing 670 relative to handle proximal end 702 may be configured to retract flexible housing tube 310 relative to handle proximal end 702. Illustratively, a retraction of actuation mechanism control 630 relative to actuation mechanism control guide proximal end 647 may be configured to retract flexible housing tube 310 relative to handle proximal end 702. In one or more embodiments, a refraction of flexible housing tube 310 relative to handle proximal end 702 may be configured to retract flexible housing tube 310 relative to wire 810. Illustratively, a portion of wire 810, e.g., a portion of wire 810 fixed to flexible housing tube 310, may be configured to facilitate a retraction of flexible housing tube 310 relative to wire 810. In one or more embodiments, as flexible housing tube 310 is retracted relative to wire 810, e.g., due to a retraction of actuation mechanism control 630 relative to actuation mechanism control guide proximal end 647, a portion of wire 810 may be configured to reduce a force applied to a portion of flexible housing tube 310. Illustratively, a reduction of a force applied to a portion of flexible housing tube 310 may be configured to cause flexible housing tube 310 to gradually straighten, e.g., by decompressing a portion of flexible housing tube 310. In one or more embodiments, a gradual straightening of flexible housing tube 310 may be configured to gradually straighten optic fiber 320. Illustratively, a refraction of actuation mechanism control 630 relative to handle proximal end 702 may be configured to gradually straighten optic fiber 320.

Figure 9A:
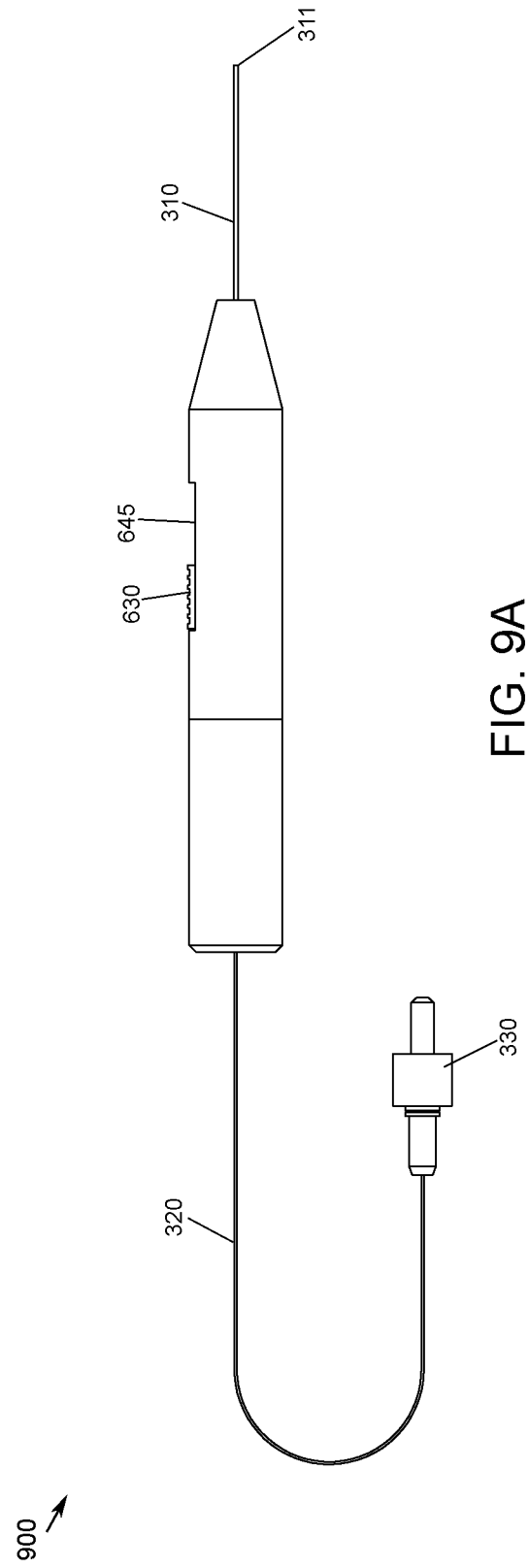
FIGS. 9A, 9B, 9C, 9D, and 9E are schematic diagrams illustrating a gradual curving of an optic fiber.

FIGS. 9A, 9B, 9C, 9D, and 9E illustrate a gradual curving of an optic fiber 320. FIG. 9A illustrates a straight optic fiber 900. In one or more embodiments, optic fiber 320 may comprise a straight optic fiber 900, e.g., when flexible housing tube 310 is fully refracted relative to handle proximal end 702. Illustratively, optic fiber 320 may comprise a straight optic fiber 900, e.g., when actuation mechanism control 630 is fully retracted relative to actuation mechanism control guide proximal end 647. In one or more embodiments, optic fiber 320 may comprise a straight optic fiber 900, e.g., when actuation mechanism 620 is fully retracted relative to handle proximal end 702. Illustratively, a line tangent to optic fiber distal end 321 may be parallel to a line tangent to flexible housing tube proximal end 312, e.g., when optic fiber 320 comprises a straight optic fiber 900.

Figure 9B:
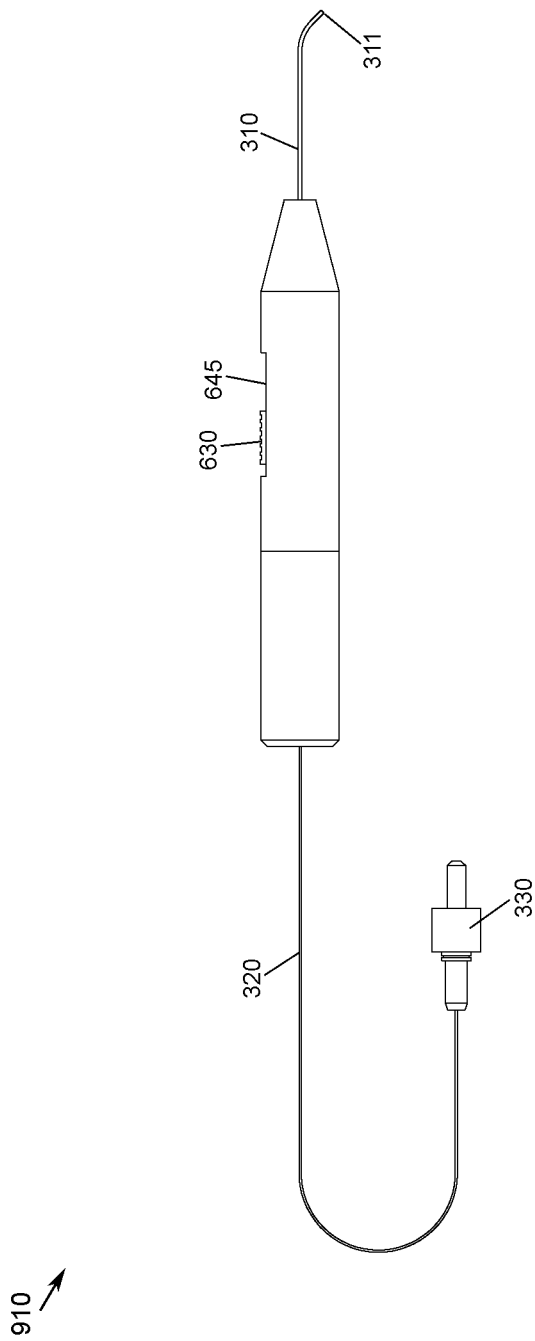

FIG. 9B illustrates an optic fiber in a first curved position 910. In one or more embodiments, an extension of actuation mechanism control 630 relative to handle proximal end 702 may be configured to gradually curve optic fiber 320 from a straight optic fiber 900 to an optic fiber in a first curved position 910. Illustratively, an extension of actuation mechanism control 630 relative to handle proximal end 702 may be configured to extend actuation mechanism 620 relative to handle proximal end 702. In one or more embodiments, an extension of actuation mechanism 620 relative to handle proximal end 702 may be configured to extend flexible housing tube 310 relative to wire 810. Illustratively, an extension of flexible housing tube 310 relative to wire 810 may be configured to apply a force to a portion of flexible housing tube 310. In one or more embodiments, an application of a force to a portion of flexible housing tube 310 may be configured to cause flexible housing tube 310 to gradually curve, e.g., by compressing a portion of flexible housing tube 310. Illustratively, a gradual curving of flexible housing tube 310 may be configured to gradually curve optic fiber 320, e.g., from a straight optic fiber 900 to an optic fiber in a first curved position 910. In one or more embodiments, a line tangent to optic fiber distal end 321 may intersect a line tangent to flexible housing tube proximal end 312 at a first angle, e.g., when optic fiber 320 comprises an optic fiber in a first curved position 910. Illustratively, the first angle may comprise any angle greater than zero degrees. For example, the first angle may comprise a 45 degree angle.

Figure 9C:
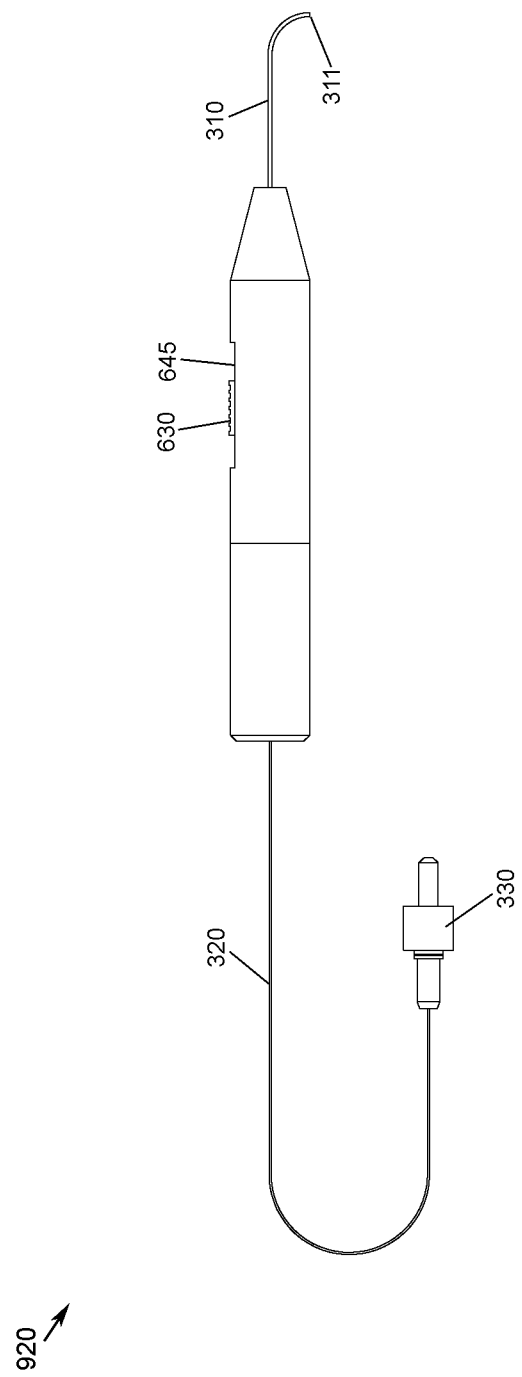

FIG. 9C illustrates an optic fiber in a second curved position 920. In one or more embodiments, an extension of actuation mechanism control 630 relative to handle proximal end 702 may be configured to gradually curve optic fiber 320 from an optic fiber in a first curved position 910 to an optic fiber in a second curved position 920. Illustratively, an extension of actuation mechanism control 630 relative to handle proximal end 702 may be configured to extend actuation mechanism 620 relative to handle proximal end 702. In one or more embodiments, an extension of actuation mechanism 620 relative to handle proximal end 702 may be configured to extend flexible housing tube 310 relative to wire 810. Illustratively, an extension of flexible housing tube 310 relative to wire 810 may be configured to apply a force to a portion of flexible housing tube 310. In one or more embodiments, an application of a force to a portion of flexible housing tube 310 may be configured to cause flexible housing tube 310 to gradually curve, e.g., by compressing a portion of flexible housing tube 310. Illustratively, a gradual curving of flexible housing tube 310 may be configured to gradually curve optic fiber 320, e.g., from an optic fiber in a first curved position 910 to an optic fiber in a second curved position 920. In one or more embodiments, a line tangent to optic fiber distal end 321 may intersect a line tangent to flexible housing tube proximal end 312 at a second angle, e.g., when optic fiber 320 comprises an optic fiber in a second curved position 920. Illustratively, the second angle may comprise any angle greater than the first angle. For example, the second angle may comprise a 90 degree angle.

Figure 9D:
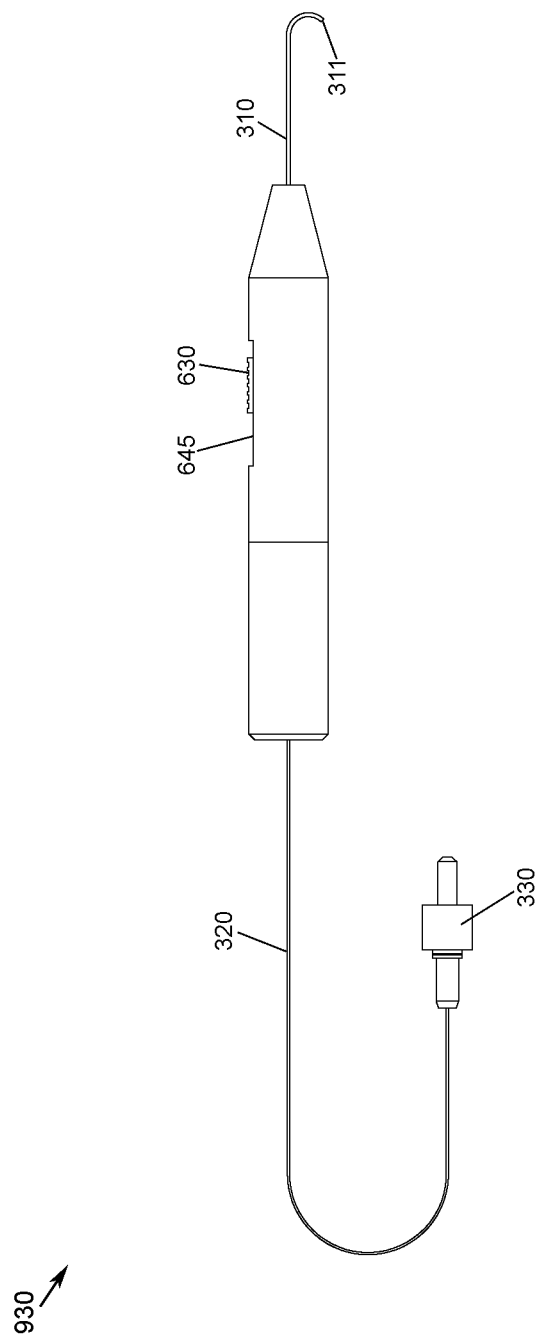

FIG. 9D illustrates an optic fiber in a third curved position 930. In one or more embodiments, an extension of actuation mechanism control 630 relative to handle proximal end 702 may be configured to gradually curve optic fiber 320 from an optic fiber in a second curved position 920 to an optic fiber in a third curved position 930. Illustratively, an extension of actuation mechanism control 630 relative to handle proximal end 702 may be configured to extend actuation mechanism 620 relative to handle proximal end 702. In one or more embodiments, an extension of actuation mechanism 620 relative to handle proximal end 702 may be configured to extend flexible housing tube 310 relative to wire 810. Illustratively, an extension of flexible housing tube 310 relative to wire 810 may be configured to apply a force to a portion of flexible housing tube 310. In one or more embodiments, an application of a force to a portion of flexible housing tube 310 may be configured to cause flexible housing tube 310 to gradually curve, e.g., by compressing a portion of flexible housing tube 310. Illustratively, a gradual curving of flexible housing tube 310 may be configured to gradually curve optic fiber 320, e.g., from an optic fiber in a second curved position 920 to an optic fiber in a third curved position 930. In one or more embodiments, a line tangent to optic fiber distal end 321 may intersect a line tangent to flexible housing tube proximal end 312 at a third angle, e.g., when optic fiber 320 comprises an optic fiber in a third curved position 930. Illustratively, the third angle may comprise any angle greater than the second angle. For example, the third angle may comprise a 135 degree angle.

Figure 9E:
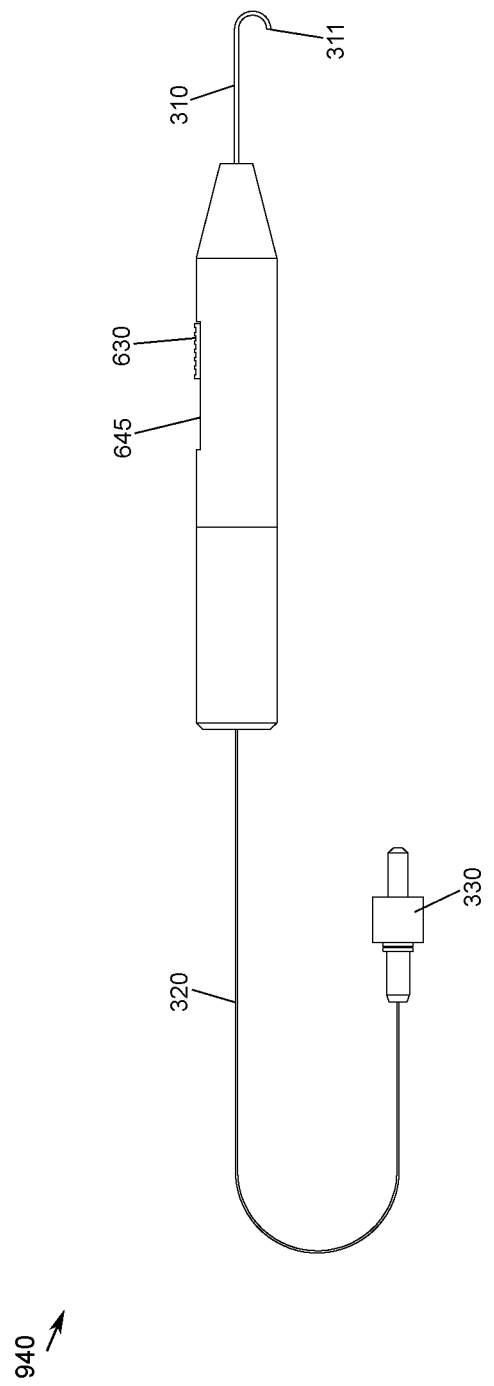

FIG. 9E illustrates an optic fiber in a fourth curved position 940. In one or more embodiments, an extension of actuation mechanism control 630 relative to handle proximal end 702 may be configured to gradually curve optic fiber 320 from an optic fiber in a third curved position 930 to an optic fiber in a fourth curved position 940. Illustratively, an extension of actuation mechanism control 630 relative to handle proximal end 702 may be configured to extend actuation mechanism 620 relative to handle proximal end 702. In one or more embodiments, an extension of actuation mechanism 620 relative to handle proximal end 702 may be configured to extend flexible housing tube 310 relative to wire 810. Illustratively, an extension of flexible housing tube 310 relative to wire 810 may be configured to apply a force to a portion of flexible housing tube 310. In one or more embodiments, an application of a force to a portion of flexible housing tube 310 may be configured to cause flexible housing tube 310 to gradually curve, e.g., by compressing a portion of flexible housing tube 310. Illustratively, a gradual curving of flexible housing tube 310 may be configured to gradually curve optic fiber 320, e.g., from an optic fiber in a third curved position 930 to an optic fiber in a fourth curved position 940. In one or more embodiments, a line tangent to optic fiber distal end 321 may be parallel to a line tangent to flexible housing tube proximal end 312, e.g., when optic fiber 320 comprises an optic fiber in a fourth curved position 940.

In one or more embodiments, one or more properties of a steerable laser probe may be adjusted to attain one or more desired steerable laser probe features. For example, a length that flexible housing tube distal end 311 extends from actuation mechanism distal end 621 may be adjusted to vary an amount of extension of actuation mechanism control 630 relative to handle proximal end 702 configured to curve flexible housing tube 310 to a particular curved position. In one or more embodiments, a stiffness of flexible housing tube 310 may be adjusted to vary an amount of extension of actuation mechanism control 630 relative to handle proximal end 702 configured to curve flexible housing tube 310 to a particular curved position. Illustratively, flexible housing tube 310 may comprise a solid tube structure. In one or more embodiments, flexible housing tube 310 may comprise one or more apertures, e.g., configured to vary a stiffness of flexible housing tube 310. Illustratively, a material comprising flexible housing tube 310 may be adjusted to vary an amount of extension of actuation mechanism control 630 relative to handle proximal end 702 configured to curve flexible housing tube 310 to a particular curved position. In one or more embodiments, a stiffness of flexible housing tube 310 may be adjusted to vary a bend radius of flexible housing tube 310. For example, a stiffness of flexible housing tube 310 may be adjusted to vary a radius of curvature of flexible housing tube 310, e.g., when flexible housing tube 310 is in a particular curved position.

In one or more embodiments, a geometry of actuation mechanism 620 may be adjusted to vary an amount of extension of actuation mechanism control 630 relative to handle proximal end 702 configured to curve flexible housing tube 310 to a particular curved position. Illustratively, a geometry of actuation mechanism guide 650 may be adjusted to vary an amount of extension of actuation mechanism control 630 relative to handle proximal end 702 configured to curve flexible housing tube 310 to a particular curved position. In one or more embodiments, a geometry of handle end cap 610 or a geometry of handle base 640 may be adjusted to vary an amount of extension of actuation mechanism control 630 relative to handle proximal end 702 configured to curve flexible housing tube 310 to a particular curved position. Illustratively, one or more locations within flexible housing tube 310 wherein wire 810 may be fixed to a portion of flexible housing tube 310 may be adjusted to vary an amount of extension of actuation mechanism control 630 relative to handle proximal end 702 configured to curve flexible housing tube 310 to a particular curved position.

In one or more embodiments, at least a portion of optic fiber 320 may be enclosed in an optic fiber sleeve configured to, e.g., protect optic fiber 320, vary a stiffness of optic fiber 320, vary an optical property of optic fiber 320, etc. Illustratively, optic fiber 320 may comprise a buffer, a cladding disposed in the buffer, and a core disposed in the cladding. In one or more embodiments, at least a portion of optic fiber 320 may comprise a buffer configured to protect an optical property of optic fiber 320. Illustratively, at least a portion of optic fiber 320 may comprise a buffer configured to protect an optical layer of optic fiber 320, e.g., the buffer may protect an optical layer of a curved portion of optic fiber 320. In one or more embodiments, at least a portion of optic fiber 320 may comprise a polyimide buffer configured to protect an optical property of optic fiber 320. For example, at least a portion of optic fiber 320 may comprise a Kapton buffer configured to protect an optical property of optic fiber 320.

Illustratively, wire 810 may be fixed to flexible housing tube 310 at a plurality of fixation points, e.g., to vary one or more properties of a steerable laser probe. In one or more embodiments, a length of wire 810 may be adjusted to vary an amount of extension of actuation mechanism control 630 relative to handle proximal end 702 configured to curve flexible housing tube 310 to a particular curved position. Illustratively, a steerable laser probe may comprise one or more redundant wires 810. In one or more embodiments, one or more redundant wires 810 may be configured to maintain a particular curved position of flexible housing tube 310, e.g., in the event that wire 810 breaks. Illustratively, one or more redundant wires 810 may be configured to maintain a particular curved position of flexible housing tube 310, e.g., in the event that a wire 810 fixation means fails. In one or more embodiments, one or more redundant wires 810 may be configured to maintain a particular curved position of flexible housing tube 310, e.g., in the event that wire 810 is no longer configured to maintain the particular curved position of flexible housing tube 310. Illustratively, one or more redundant wires 810 may be configured to maintain a particular curved position of flexible housing tube 310 wherein wire 810 is also configured to maintain the particular curved position of flexible housing tube 310.

Illustratively, a steerable laser probe may be configured to indicate, e.g., to a surgeon, a direction that optic fiber 320 may curve, e.g., due to an extension of actuation mechanism control 630 relative to handle proximal end 702. In one or more embodiments, a portion of a steerable laser probe, e.g., handle 700, may be marked in a manner configured to indicate a direction that optic fiber 320 may curve. For example, a portion of flexible housing tube 310 may comprise a mark configured to indicate a direction that optic fiber 320 may curve. Illustratively, flexible housing tube 310 may comprise a slight curve, e.g., a curve less than 7.5 degrees, when actuation mechanism control 630 is fully refracted relative to handle proximal end 702. In one or more embodiments, flexible housing tube 310 may comprise a slight curve configured to indicate a direction that optic fiber 320 may curve, e.g., due to an extension of actuation mechanism control 630 relative to handle proximal end 702.

Illustratively, handle base 640 may comprise a plurality of actuation mechanism control guides 645. In one or more embodiments, actuation mechanism 620 may comprise a plurality of actuation mechanism controls 630. For example, handle 700 may comprise a first actuation mechanism control 630 disposed within a first actuation mechanism control guide 645 and a second actuation mechanism control 630 disposed in a second actuation mechanism control guide 645. Illustratively, an extension of either the first actuation mechanism control 630 or the second actuation mechanism control 630 relative to handle proximal end 702 may be configured to extend actuation mechanism 620 relative to handle proximal end 702. In one or more embodiments, a retraction of either the first actuation mechanism control 630 or the second actuation mechanism control 630 relative to handle proximal end 702 may be configured to retract actuation mechanism 620 relative to handle proximal end 702. Illustratively, handle 700 may comprise a third actuation mechanism control 630 disposed in a third actuation mechanism control guide 645. In one or more embodiments, an extension of either the first actuation mechanism control 630, the second actuation mechanism control 630, or the third actuation mechanism control 630 relative to handle proximal end 702 may be configured to extend actuation mechanism 620 relative to handle proximal end 702. Illustratively, a retraction of either the first actuation mechanism control 630, the second actuation mechanism control 630, or the third actuation mechanism control 630 relative to handle proximal end 702 may be configured to retract actuation mechanism 620 relative to handle proximal end 702.

In one or more embodiments, a steerable laser probe may comprise a pressure mechanism configured to provide a force. Illustratively, a pressure mechanism may be disposed within pressure mechanism housing 680. In one or more embodiments, a pressure mechanism may be configured to provide a constant force. Illustratively, a pressure mechanism may be configured to provide a variable force. In one or more embodiments, a pressure mechanism may be configured to provide a resistive force, e.g., to resist an extension of actuation mechanism 620 relative to handle proximal end 702. Illustratively, a pressure mechanism may be configured to provide a facilitating force, e.g., to facilitate a retraction of actuation mechanism 620 relative to handle proximal end 702. In one or more embodiments, a pressure mechanism may comprise a spring or a coil. Illustratively, a pressure mechanism may comprise a pneumatic system or any system configured to provide a force.

Figure 10A:
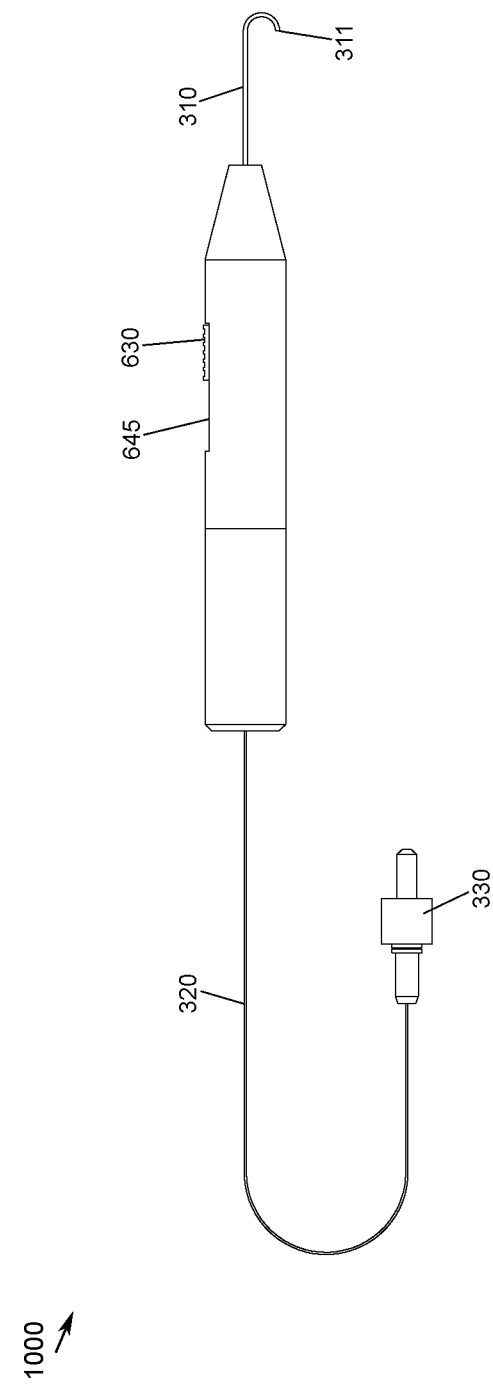
FIGS. 10A, 10B, 10C, 10D, and 10E are schematic diagrams illustrating a gradual straightening of an optic fiber.

FIGS. 10A, 10B, 10C, 10D, and 10E illustrate a gradual straightening of an optic fiber 320. FIG. 10A illustrates a fully curved optic fiber 1000. In one or more embodiments, optic fiber 320 may comprise a fully curved optic fiber 1000, e.g., when flexible housing tube 310 is fully extended relative to handle proximal end 702. Illustratively, optic fiber 320 may comprise a fully curved optic fiber 1000, e.g., when actuation mechanism control 630 is fully extended relative to actuation mechanism control guide proximal end 647. In one or more embodiments, optic fiber 320 may comprise a fully curved optic fiber 1000, e.g., when actuation mechanism 620 is fully extended relative to handle proximal end 702. Illustratively, a line tangent to optic fiber distal end 321 may be parallel to a line tangent to flexible housing tube proximal end 312, e.g., when optic fiber 320 comprises a fully curved optic fiber 1000.

Figure 10B:
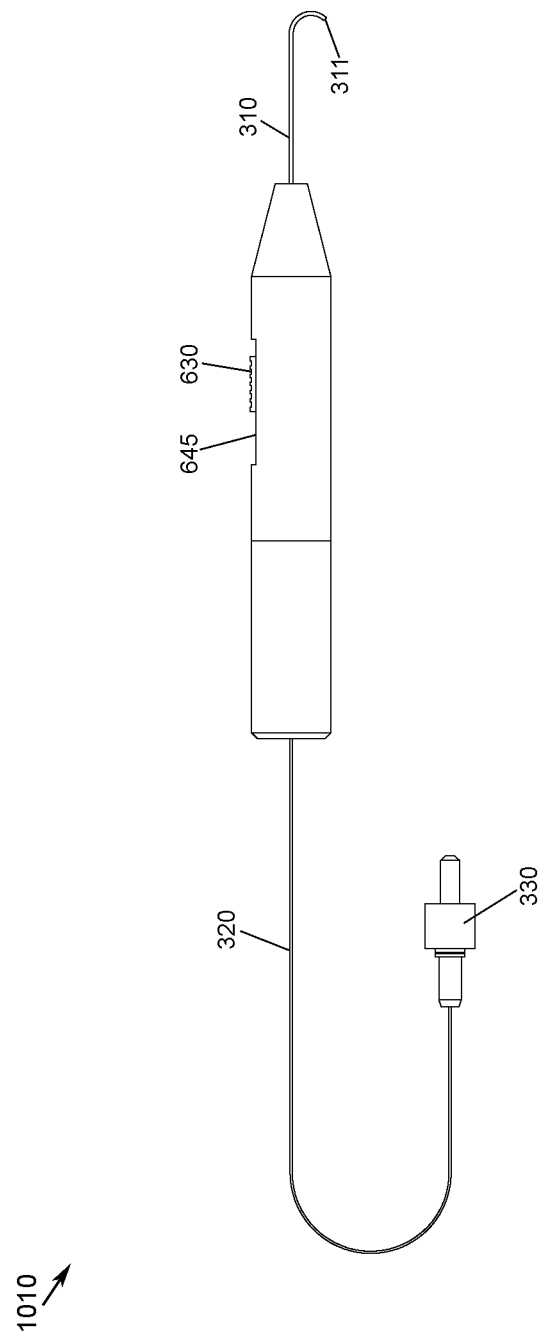

FIG. 10B illustrates an optic fiber in a first partially straightened position 1010. In one or more embodiments, a retraction of actuation mechanism control 630 relative to handle proximal end 702 may be configured to gradually straighten optic fiber 320 from a fully curved optic fiber 1000 to an optic fiber in a first partially straightened position 1010. Illustratively, a retraction of actuation mechanism control 630 relative to handle proximal end 702 may be configured to retract actuation mechanism 620 relative to handle proximal end 702. In one or more embodiments, a retraction of actuation mechanism 620 relative to handle proximal end 702 may be configured to retract flexible housing tube 310 relative to wire 810. Illustratively, a retraction of flexible housing tube 310 relative to wire 810 may be configured to reduce a force applied to a portion of flexible housing tube 310. In one or more embodiments, a reduction of a force applied to a portion of flexible housing tube 310 may be configured to cause flexible housing tube 310 to gradually straighten, e.g., by decompressing a portion of flexible housing tube 310. Illustratively, a gradual straightening of flexible housing tube 310 may be configured to gradually straighten optic fiber 320, e.g., from a fully curved optic fiber 1000 to an optic fiber in a first partially straightened position 1010. In one or more embodiments, a line tangent to optic fiber distal end 321 may intersect a line tangent to flexible housing tube proximal end 312 at a first partially straightened angle, e.g., when optic fiber 320 comprises an optic fiber in a first partially straightened position 1010. Illustratively, the first partially straightened angle may comprise any angle less than 180 degrees. For example, the first partially straightened angle may comprise a 135 degree angle.

Figure 10C:
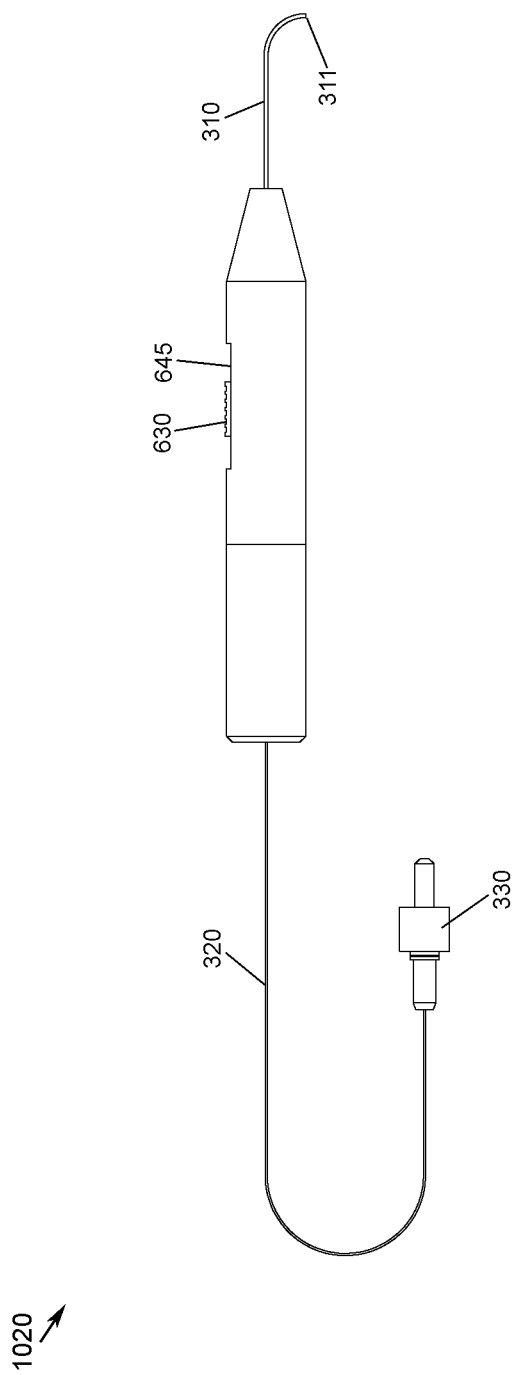

FIG. 10C illustrates an optic fiber in a second partially straightened position 1020. In one or more embodiments, a retraction of actuation mechanism control 630 relative to handle proximal end 702 may be configured to gradually straighten optic fiber 320 from an optic fiber in a first partially straightened position 1010 to an optic fiber in a second partially straightened position 1020. Illustratively, a retraction of actuation mechanism control 630 relative to handle proximal end 702 may be configured to retract actuation mechanism 620 relative to handle proximal end 702. In one or more embodiments, a retraction of actuation mechanism 620 relative to handle proximal end 702 may be configured to retract flexible housing tube 310 relative to wire 810. Illustratively, a refraction of flexible housing tube 310 relative to wire 810 may be configured to reduce a force applied to a portion of flexible housing tube 310. In one or more embodiments, a reduction of a force applied to a portion of flexible housing tube 310 may be configured to cause flexible housing tube 310 to gradually straighten, e.g., by decompressing a portion of flexible housing tube 310. Illustratively, a gradual straightening of flexible housing tube 310 may be configured to gradually straighten optic fiber 320, e.g., from an optic fiber in a first partially straightened position 1010 to an optic fiber in a second partially straightened position 1020. In one or more embodiments, a line tangent to optic fiber distal end 321 may intersect a line tangent to flexible housing tube proximal end 312 at a second partially straightened angle, e.g., when optic fiber 320 comprises an optic fiber in a second partially straightened position 1020. Illustratively, the second partially straightened angle may comprise any angle less than the first partially straightened angle. For example, the second partially straightened angle may comprise a 90 degree angle.

Figure 10D:
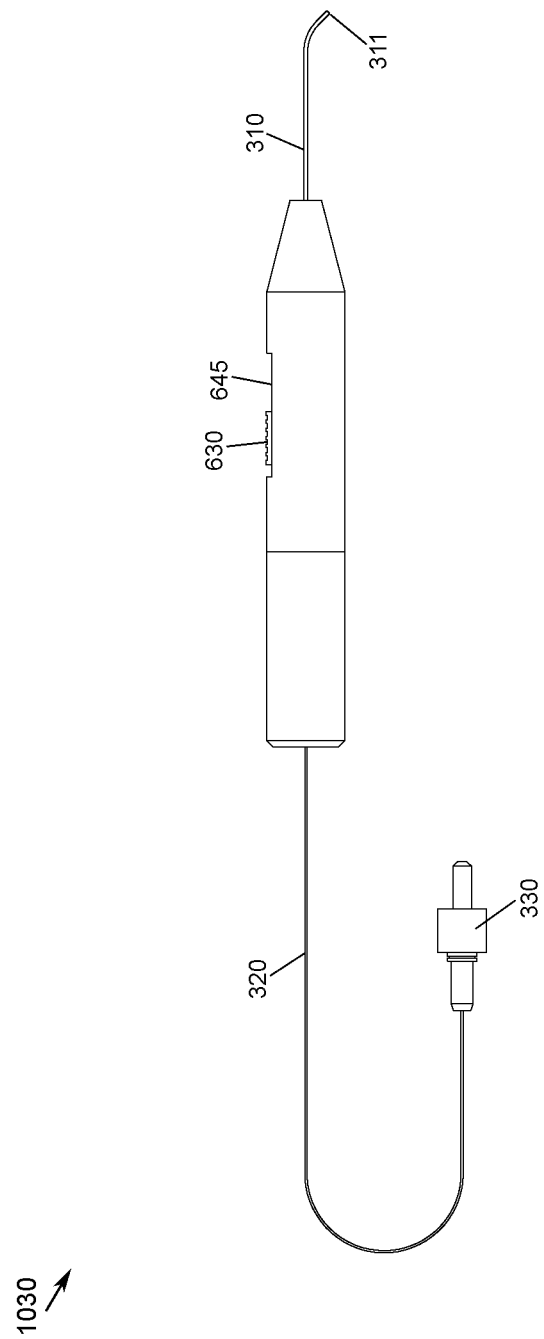

FIG. 10D illustrates an optic fiber in a third partially straightened position 1030. In one or more embodiments, a retraction of actuation mechanism control 630 relative to handle proximal end 702 may be configured to gradually straighten optic fiber 320 from an optic fiber in a second partially straightened position 1020 to an optic fiber in a third partially straightened position 1030. Illustratively, a retraction of actuation mechanism control 630 relative to handle proximal end 702 may be configured to retract actuation mechanism 620 relative to handle proximal end 702. In one or more embodiments, a retraction of actuation mechanism 620 relative to handle proximal end 702 may be configured to retract flexible housing tube 310 relative to wire 810. Illustratively, a retraction of flexible housing tube 310 relative to wire 810 may be configured to reduce a force applied to a portion of flexible housing tube 310. In one or more embodiments, a reduction of a force applied to a portion of flexible housing tube 310 may be configured to cause flexible housing tube 310 to gradually straighten, e.g., by decompressing a portion of flexible housing tube 310. Illustratively, a gradual straightening of flexible housing tube 310 may be configured to gradually straighten optic fiber 320, e.g., from an optic fiber in a second partially straightened position 1020 to an optic fiber in a third partially straightened position 1030. In one or more embodiments, a line tangent to optic fiber distal end 321 may intersect a line tangent to flexible housing tube proximal end 312 at a third partially straightened angle, e.g., when optic fiber 320 comprises an optic fiber in a third partially straightened position 1030. Illustratively, the third partially straightened angle may comprise any angle less than the second partially straightened angle. For example, the third partially straightened angle may comprise a 45 degree angle.

Figure 10E:
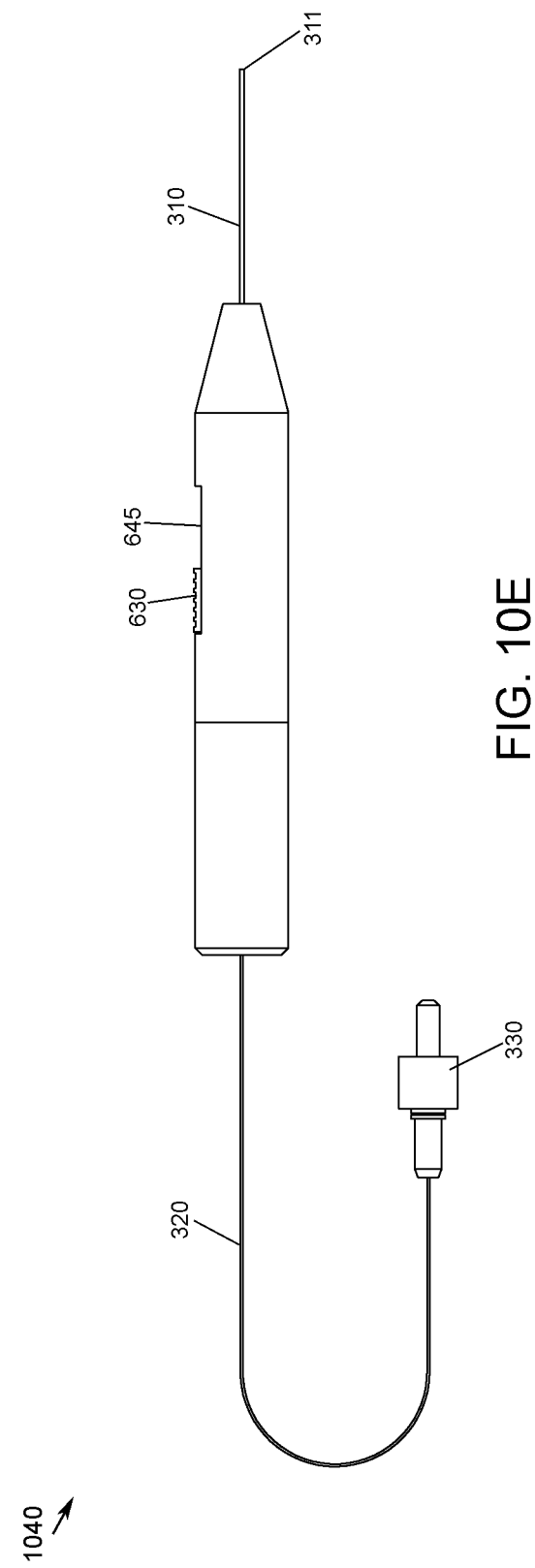

FIG. 10E illustrates an optic fiber in a fully straightened position 1040. In one or more embodiments, a retraction of actuation mechanism control 630 relative to handle proximal end 702 may be configured to gradually straighten optic fiber 320 from an optic fiber in a third partially straightened position 1030 to an optic fiber in a fully straightened position 1040. Illustratively, a retraction of actuation mechanism control 630 relative to handle proximal end 702 may be configured to retract actuation mechanism 620 relative to handle proximal end 702. In one or more embodiments, a retraction of actuation mechanism 620 relative to handle proximal end 702 may be configured to retract flexible housing tube 310 relative to wire 810. Illustratively, a refraction of flexible housing tube 310 relative to wire 810 may be configured to reduce a force applied to a portion of flexible housing tube 310. In one or more embodiments, a reduction of a force applied to a portion of flexible housing tube 310 may be configured to cause flexible housing tube 310 to gradually straighten, e.g., by decompressing a portion of flexible housing tube 310. Illustratively, a gradual straightening of flexible housing tube 310 may be configured to gradually straighten optic fiber 320, e.g., from an optic fiber in a third partially straightened position 1030 to an optic fiber in a fully straightened position 1040. In one or more embodiments, a line tangent to optic fiber distal end 321 may be parallel to a line tangent to flexible housing tube proximal end 312, e.g., when optic fiber 320 comprises an optic fiber in a fully straightened position 1040.

Illustratively, a surgeon may aim optic fiber distal end 321 at any of a plurality of targets within an eye, e.g., to perform a photocoagulation procedure, to illuminate a surgical target site, etc. In one or more embodiments, a surgeon may aim optic fiber distal end 321 at any target within a particular transverse plane of the inner eye by, e.g., rotating handle 700 to orient flexible housing tube 310 in an orientation configured to cause a curvature of flexible housing tube 310 within the particular transverse plane of the inner eye and varying an amount of extension of actuation mechanism control 630 relative to handle proximal end 702. Illustratively, a surgeon may aim optic fiber distal end 321 at any target within a particular sagittal plane of the inner eye by, e.g., rotating handle 700 to orient flexible housing tube 310 in an orientation configured to cause a curvature of flexible housing tube 310 within the particular sagittal plane of the inner eye and varying an amount of extension of actuation mechanism control 630 relative to handle proximal end 702. In one or more embodiments, a surgeon may aim optic fiber distal end 321 at any target within a particular frontal plane of the inner eye by, e.g., varying an amount of extension of actuation mechanism control 630 relative to handle proximal end 702 to orient a line tangent to optic fiber distal end 321 wherein the line tangent to optic fiber distal end 321 is within the particular frontal plane of the inner eye and rotating handle 700. Illustratively, a surgeon may aim optic fiber distal end 321 at any target located outside of the particular transverse plane, the particular sagittal plane, and the particular frontal plane of the inner eye, e.g., by varying a rotational orientation of handle 700 and varying an amount of extension of actuation mechanism control 630 relative to handle proximal end 702. In one or more embodiments, a surgeon may aim optic fiber distal end 321 at any target of a plurality of targets within an eye, e.g., without increasing a length of a portion of a steerable laser probe within the eye. Illustratively, a surgeon may aim optic fiber distal end 321 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:

1. An instrument comprising:
    a handle having a handle distal end and a handle proximal end;
    an actuation mechanism of the handle having an actuation mechanism distal end and an actuation mechanism proximal end;
    an inner bore of the actuation mechanism;
    a flexible housing tube housing of the actuation mechanism;
    an actuation mechanism control of the actuation mechanism having an actuation mechanism control distal end and an actuation mechanism control proximal end;
    a handle base of the handle having a handle base distal end and a handle base proximal end;
    a flexible housing tube guide of the handle base;
    a handle end cap interface of the handle base;
    an actuation mechanism control guide of the handle base having an actuation mechanism control guide distal end and an actuation mechanism control guide proximal end;
    an actuation mechanism guide of the handle base;
    a handle end cap of the handle having a handle end cap distal end, a handle end cap proximal end, a handle base interface, and a handle base housing, the handle base disposed in the handle base housing wherein the handle end cap interface is adjacent to the handle base interface and wherein the actuation mechanism is disposed in the handle end cap and the handle base wherein the actuation mechanism control is disposed in the actuation mechanism control guide, the actuation mechanism distal end is disposed in handle base, and the actuation mechanism proximal end is disposed in the handle end cap;
    a flexible housing tube having a flexible housing tube distal end and a flexible housing tube proximal end, the flexible housing tube configured for an insertion into a cannula to perform an ophthalmic surgical procedure wherein the flexible housing tube is disposed in the flexible housing tube housing and the flexible housing tube guide; and
    an optic fiber disposed within the inner bore of the actuation mechanism and the flexible housing tube, the optic fiber configured to transmit a laser light.

2. The instrument of claim 1 wherein the flexible housing tube is a solid tube.

3. The instrument of claim 2 wherein an extension of the actuation mechanism control relative to the handle proximal end is configured to gradually curve the optic fiber.

4. The instrument of claim 3 wherein the extension of the actuation mechanism control relative to the handle proximal end is configured to gradually curve the flexible housing tube.

5. The instrument of claim 4 wherein the extension of the actuation mechanism control relative to the handle proximal end is configured to extend the flexible housing tube relative to the optic fiber.

6. The instrument of claim 2 wherein a retraction of the actuation mechanism control relative to the handle proximal end is configured to gradually straighten the optic fiber.

7. The instrument of claim 6 wherein the retraction of the actuation mechanism control relative to the handle proximal end is configured to gradually straighten the flexible housing tube.

8. The instrument of claim 7 wherein the retraction of the actuation mechanism control relative to the handle proximal end is configured to retract the flexible housing tube relative to the optic fiber.

9. The instrument of claim 2 further comprising:
    a wire disposed within the inner bore of the handle and the flexible housing tube;
    a first portion of the wire fixed in a position relative to the handle proximal end;
    and a second portion of the wire fixed to the flexible housing tube.

10. The instrument of claim 9 wherein an extension of the actuation mechanism control relative to the handle proximal end is configured to gradually curve the optic fiber.

11. The instrument of claim 10 wherein the extension of the actuation mechanism control relative to the handle proximal end is configured to gradually curve the flexible housing tube.

12. The instrument of claim 11 wherein the extension of the actuation mechanism control relative to the handle proximal end is configured to extend the flexible housing tube relative to the wire.

13. The instrument of claim 9 wherein a retraction of the actuation mechanism control relative to the handle proximal end is configured to gradually straighten the optic fiber.

14. The instrument of claim 13 wherein the retraction of the actuation mechanism control relative to the handle proximal end is configured to gradually straighten the flexible housing tube.

15. The instrument of claim 14 wherein the retraction of the actuation mechanism control relative to the handle proximal end is configured to retract the flexible housing tube relative to the wire.

16. The instrument of claim 15 wherein the wire is configured to facilitate a retraction of the flexible housing tube relative to the wire.

17. The instrument of claim 9 further comprising:
a redundant wire disposed within the inner bore of the handle and the flexible housing tube, the redundant wire configured to maintain a particular curved position of the flexible housing tube.

18. The instrument of claim 1 further comprising:
a pressure mechanism housing of the handle base.

19. The instrument of claim 1 wherein the flexible housing tube is manufactured from nitinol.

20. The instrument of claim 1 wherein the flexible housing tube has an ultimate tensile strength in a range of 1000 to 1100 MPa.

* * * * *